(12) United States Patent
Frank et al.

(10) Patent No.: US 11,426,102 B2
(45) Date of Patent: Aug. 30, 2022

(54) DIABETES PREDICTION USING GLUCOSE MEASUREMENTS AND MACHINE LEARNING

(71) Applicant: DexCom, Inc., San Diego, CA (US)

(72) Inventors: Spencer Frank, San Diego, CA (US); David Price, Carlsbad, CA (US); Chuck Stroyeck, Carlsbad, CA (US); Kazanna Calais Hames, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 143 days.

(21) Appl. No.: 16/917,421

(22) Filed: Jun. 30, 2020

(65) Prior Publication Data

US 2021/0401330 A1 Dec. 30, 2021

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/0024* (2013.01); *A61B 5/14503* (2013.01);
(Continued)

(58) Field of Classification Search
CPC ........ G16H 10/60; G16H 15/00; G16H 50/00; G16H 50/20; G16H 50/30; G16H 50/50;
(Continued)

(56) References Cited

U.S. PATENT DOCUMENTS

| | | | | |
|---|---|---|---|---|
| 8,538,703 B2 * | 9/2013 | Kovatchev | ......... | A61B 5/14546 702/19 |
| 2005/0159656 A1 * | 7/2005 | Hockersmith | ..... | A61B 5/14532 600/315 |

(Continued)

FOREIGN PATENT DOCUMENTS

| | | | | |
|---|---|---|---|---|
| WO | WO-2004043230 A2 * | 5/2004 | ............. | G16H 50/70 |
| WO | WO-2019143407 A1 * | 7/2019 | ......... | A61B 5/14532 |
| WO | WO-2020257158 A1 * | 12/2020 | ......... | A61B 5/14532 |

*Primary Examiner* — Eric F Winakur
*Assistant Examiner* — Alice Ling Zou
(74) *Attorney, Agent, or Firm* — FIG. 1 Patents

(57) ABSTRACT

Diabetes prediction using glucose measurements and machine learning is described. In one or more implementations, the observation analysis platform includes a machine learning model trained using historical glucose measurements and historical outcome data of a user population to predict a diabetes classification for an individual user. The historical glucose measurements of the user population may be provided by glucose monitoring devices worn by users of the user population, while the historical outcome data includes one or more diagnostic measurements obtained from sources independent of the glucose monitoring devices. Once trained, the machine learning model predicts a diabetes classification for a user based on glucose measurements collected by a wearable glucose monitoring device during an observation period spanning multiple days. The predicted diabetes classification may then be output, such as by generating one or more notifications or user interfaces based on the classification.

37 Claims, 11 Drawing Sheets

(51) Int. Cl.
*G16H 50/20* (2018.01)
*A61B 5/1486* (2006.01)
*G16H 20/00* (2018.01)
*G16H 10/60* (2018.01)
*G16H 15/00* (2018.01)

(52) U.S. Cl.
CPC ........ *A61B 5/14865* (2013.01); *A61B 5/6847* (2013.01); *A61B 5/7267* (2013.01); *A61B 5/7275* (2013.01); *G16H 10/60* (2018.01); *G16H 15/00* (2018.01); *G16H 20/00* (2018.01); *G16H 50/20* (2018.01)

(58) Field of Classification Search
CPC .... G16H 50/70; G16H 20/00; A61B 5/14532; A61B 5/14865; A61B 5/7264–7267; A61B 5/7271; A61B 5/7275; A61B 5/7282; A61B 5/14546; A61B 5/14735; A61B 5/1486; A61B 5/7278
See application file for complete search history.

(56) References Cited

U.S. PATENT DOCUMENTS

| | | | |
|---|---|---|---|
| 2006/0020192 A1* | 1/2006 | Brister | A61B 5/14514 600/345 |
| 2008/0147441 A1* | 6/2008 | Kil | G16H 50/30 705/2 |
| 2017/0071511 A1* | 3/2017 | Garcia | A61B 5/0031 |

* cited by examiner

DIABETES PREDICTION USING GLUCOSE MEASUREMENTS AND MACHINE LEARNING

FIELD

Diabetes prediction using glucose measurements and machine learning is described. In one or more implementations, the observation analysis platform includes a machine learning model trained using historical glucose measurements and historical outcome data of a user population to predict a diabetes classification for an individual user. The historical glucose measurements of the user population may be provided by glucose monitoring devices worn by users of the user population, while the historical outcome data includes one or more diagnostic measurements obtained from sources independent of the glucose monitoring devices. Once trained, the machine learning model predicts a diabetes classification for a user based on glucose measurements collected by a wearable glucose monitoring device during an observation period spanning multiple days. The predicted diabetes classification may then be output, such as by generating one or more notifications or user interfaces based on the classification.

BACKGROUND

Diabetes is a metabolic condition affecting hundreds of millions of people, and is one of the leading causes of death worldwide. With early detection and proper treatment, however, serious damage to the heart, blood vessels, eyes, kidneys, and nerves, due to diabetes can be largely avoided. Conventional tests for diabetes which are accepted by the clinical and regulatory communities, include Hemoglobin A1c (HbA1c), Fasting Plasma Glucose (FPG), and 2-Hour Plasma Glucose (2 Hr-PG)—both the FPG and the 2 Hr-PG are part of the Oral Glucose Tolerance Test (OGTT) but the FPG can be tested separately from the OGTT. For the FPG test, a blood sample is taken and the result is used to classify the person as being "normal" (e.g., no diabetes), or as having prediabetes or diabetes. Generally, a person is considered normal if her fasting glucose level is less than 100 mg/dL, whereas the person is classified as having prediabetes if her fasting blood glucose level is between 100 to 125 mg/dL or as having diabetes if her fasting blood glucose level greater than 126 mg/dL on two separate tests.

After measuring the person's fasting blood glucose for the FPG test, the OGTT then requires the person to drink a sugary liquid to cause a spike in the person's blood glucose level. Many people have difficulty tolerating this sugary drink, particularly women who are pregnant. The person's blood glucose levels are then tested periodically using additional blood samples for the next two hours for the 2 Hr-PG. A blood sugar level that is less than 140 mg/dL is considered "normal", whereas a reading of more than 200 mg/dL two hours after drinking the sugary drink indicates diabetes. A reading between 140 and 199 mg/dL indicates prediabetes.

Unlike the FPG and 2 Hr-PG tests of the OGTT, which each measure a person's blood glucose level at a single point in time, the HbA1c test measures an average glucose level of the user over the previous two to three months. Rather than directly measuring glucose, however, the HbA1c test measures the percentage of glucose that is attached to hemoglobin. Note that when glucose builds up in a person's blood, it attaches to hemoglobin, the oxygen-carrying protein in red blood cells. Red blood cells live for approximately two to three months in a person, and thus the HbA1c test shows the average level of glucose in the blood over the previous two to three months. Unlike the FPG and 2 Hr-PG tests, the person does not need to be in a fasted state when the HbA1c test is administered. However, similar to the FPG and 2 Hr-PG tests, to measure a person's HbA1c level, a blood sample must be taken from the person and used to produce a reading. An HbA1c level of 6.5 percent or higher on two separate tests indicates that the person has diabetes, while an HbA1c level between 5.7 and 6.4 percent generally indicates that the person has prediabetes. An HbA1c level below 5.7 percent is considered normal.

Each of these conventional tests administered to screen for, or diagnose, diabetes have a variety of drawbacks which often leads to improper diagnosis. Conventional diabetes tests are often inaccurate because a given test administered to an individual on different days may result in inconsistent diagnoses due to various external factors which may cause glucose levels to fluctuate, such as sickness, stress, increased exercise, or pregnancy. In contrast, even though the HbA1c test measures an average glucose level over a previous two to three months, the HbA1c test results are greatly impacted by the user's blood glucose levels in the weeks leading up the test. As such, HbA1c test results can be greatly affected by changes in blood properties during the three-month time period, such as due to pregnancy or illness. Additionally, because the HbA1c test is not a direct measure of blood glucose, such tests may be inaccurate for people with various blood conditions such as anemia or having an uncommon form of hemoglobin.

Additionally, such conventional tests often have poor concordance. In other words, these tests do not necessarily detect diabetes in the same individuals. This lack of consistency between test types may lead to an inaccurate diagnosis or failure to determine a proper treatment plan. For example, a user may have a high fasting glucose but an HbA1c score within the normal range. In such scenarios, different doctors may reach different conclusions regarding whether or not the user has diabetes as well as the type of treatment plan for the user.

Finally, there are also a variety of limitations and drawbacks of administering these tests to different people, such as pregnant women. For example, these conventional diabetes tests require the user to visit a doctor's office or lab in order to take a blood sample which can be time consuming, expensive, and painful for some users. Each of these factors in combination may act to create a psychological barrier preventing users from getting tested for diabetes, thereby mitigating the benefits which may be achieved by early detection. Moreover, many of these conventional tests require the user to be in a fasted state, which can be difficult, or even dangerous, for some users including women who are pregnant.

SUMMARY

To overcome these problems, diabetes prediction using glucose measurements and machine learning is leveraged. In one or more implementations, an observation analysis platform includes a machine learning model trained using historical glucose measurements and historical outcome data of a user population to predict a diabetes classification for an individual user. The historical glucose measurements of the user population may be provided by glucose monitoring devices worn by users of the user population, while the historical outcome data includes one or more diagnostic measurements obtained from sources independent of the glucose monitoring devices. For instance, the historical outcome data may indicate whether a respective user of the user population is clinically diagnosed with diabetes or not based on one or more diagnostic measures, such as HbA1c, FPG, or 2 Hr-PG.

Once trained, the machine learning model predicts a diabetes classification for a user based on glucose measurements collected by a wearable glucose monitoring device during an observation period spanning multiple days. In particular, the machine learning model generates this prediction based on the training with the historical glucose measurements and historical outcome data of the user population. The diabetes classification may describe a state of the user during the observation period (e.g., as having one of diabetes, prediabetes, or no diabetes) or whether the user is predicted to experience adverse effects of diabetes. The predicted diabetes classification may then be output, such as by generating one or more notifications or user interfaces based on the classification, such as a report directed to a health care provider that includes the diabetes classification (e.g., that the person is predicted to have diabetes) or a notification directed to the person that instructs the person to contact his or her health care provider.

This Summary introduces a selection of concepts in a simplified form that are further described below in the Detailed Description. As such, this Summary is not intended to identify essential features of the claimed subject matter, nor is it intended to be used as an aid in determining the scope of the claimed subject matter.

BRIEF DESCRIPTION OF THE DRAWINGS

The detailed description is described with reference to the accompanying figures.

DETAILED DESCRIPTION

Overview

Figure 1:
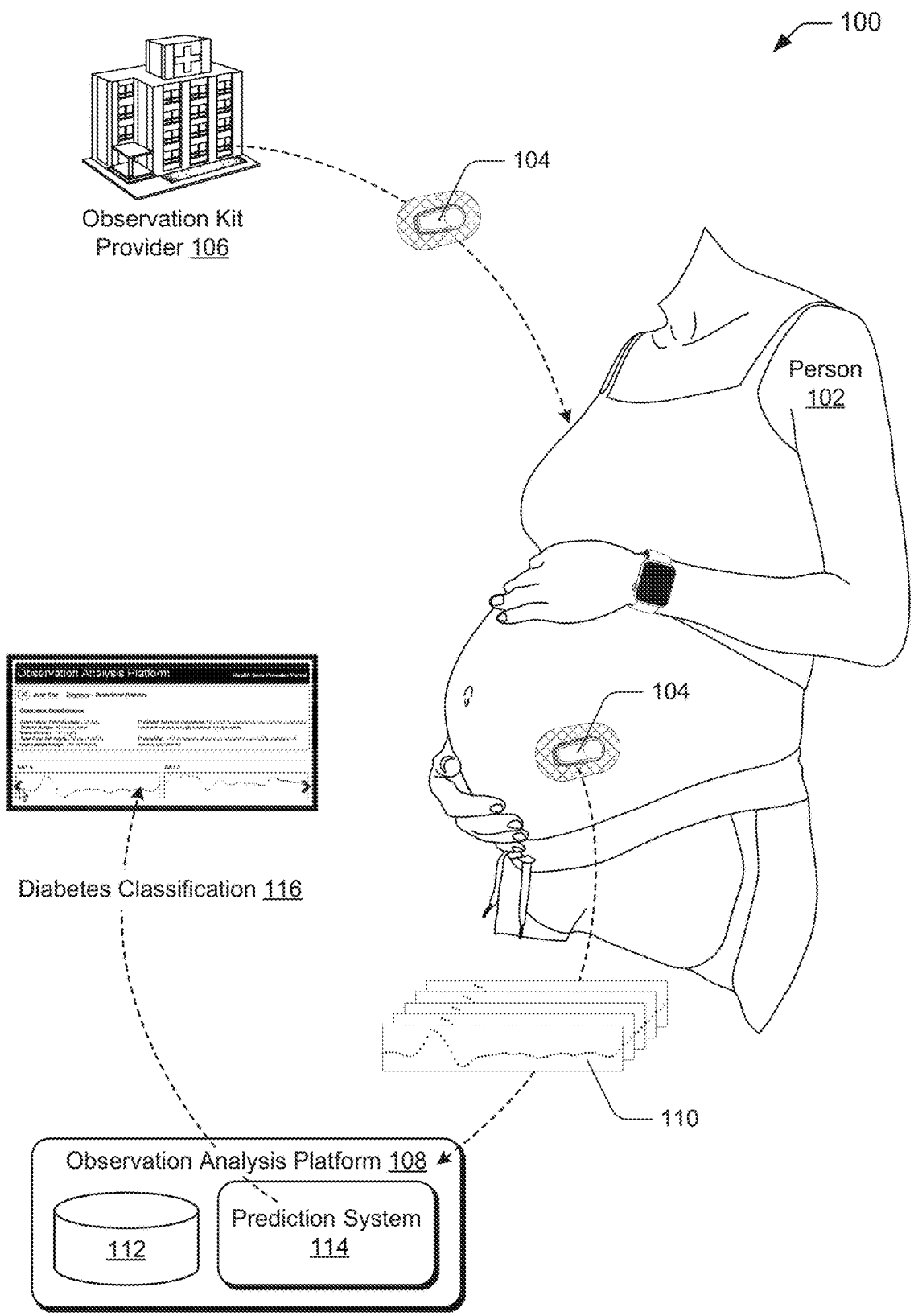
FIG. 1 is an illustration of an environment in an example of an implementation that is operable to employ techniques described herein.

Conventional tests for diabetes which are accepted by the clinical and regulatory communities, include Hemoglobin A1c (HbA1c), Fasting Plasma Glucose (FPG), and 2-Hour Plasma Glucose (2 Hr-PG)—both the FPG and the 2 Hr-PG are part of the Oral Glucose Tolerance Test (OGTT) but the FPG can be tested separately from the OGTT. Such conventional tests, however, often have poor concordance. In other words, these tests do not necessarily detect diabetes in the same individuals. A given test administered to an individual on different days may also result in inconsistent diagnoses due to the various factors which affect blood glucose levels. There are also a variety of limitations and drawbacks of administering these tests to different people, such as pregnant women.

To overcome these problems, diabetes prediction using glucose measurements and machine learning is leveraged. To classify people as having diabetes, one or more machine learning models (e.g., regression models, neural networks, reinforcement learning agents) are generated using historical glucose measurements and historical outcome data of a user population to predict a diabetes classification for an individual user. The historical glucose measurements of the user population may be provided by glucose monitoring devices worn by users of the user population. In contrast, the historical outcome data used for training may vary depending on classifications that the machine learning models are configured to output. Generally, the historical outcome data includes one or more diagnostic measures obtained from sources independent of the glucose monitoring devices. For instance, the historical outcome data may indicate whether a respective user of the user population is clinically diagnosed with diabetes or not based on one or more diagnostic measures, such as HbA1c, FPG, or 2 Hr-PG (or OGTT as a combination of FPG and 2 Hr-PG).

Regardless of the particular outcome data used, training enables the machine learning model to predict diabetes classifications based on an individual's glucose measurements collected during an observation period. In other words, the machine learning model learns to identify patterns in glucose measurements which are correlated to having diabetes or not having diabetes. The machine learning model may learn, for instance, particular features of the glucose data which are highly correlated to having diabetes or not having diabetes. Examples of features that the machine learning model may learn to correlate with the diabetes classification include, by way of example and not limitation, time over threshold measures, rate-of-change measures, observation period anomalies, and a mean or median glucose value during the observation period. Notably, many of the features that the machine learning model learns to correlate with the diabetes classification, such as the time over threshold measures and the rate-of change measures, are features that simply cannot be determined using conventional diagnostic tests which output a result based on a blood sample measured at a single point of time.

Once the machine learning model is trained, it is used to predict a diabetes classification for a user based on glucose measurements collected by a wearable glucose monitoring device worn by the user during an observation period spanning multiple days. This "diabetes classification" may in some implementations indicate whether a user has diabetes or is at risk for developing diabetes and/or indicate adverse effects that the user is predicted to experience. By way of example, a user may have his or her glucose monitored to predict whether he or she has diabetes (e.g., Type 1 diabetes, Type 2 diabetes, gestational diabetes mellitus (GDM), cystic fibrosis diabetes, and so on) or is at risk for developing diabetes (e.g., prediabetes), and/or whether she is predicted to experience adverse effects associated with diabetes (e.g., retinopathy, neuropathy, comorbidity, dysglycemia, macrosomia requiring a cesarean section, and neonatal hypoglycemia, to name just a few). In a similar fashion as diabetes classifications indicating a type of diabetes are predicted (e.g., Type 2, GDM, etc.), in one or more implementations, the machine learning model may additionally or alternately be configured to predict a type of prediabetes (e.g., impaired glucose fasting (IFG) or impaired glucose tolerance (IGT)). Alternately or additionally, the diabetes classification may correspond to a risk level of having or developing diabetes, such as high risk, low risk, or no risk. In operation, a diabetes classification predicted by the machine learning model may be used (e.g., by a health care professional) to treat the person or develop a treatment plan similarly to how the person would be treated if clinically diagnosed using conventional tests (e.g., with a type of diabetes and/or as being susceptible to experiencing adverse effects).

Unlike such conventional tests which are traditionally administered in a lab or doctor's office, however, use of the wearable glucose monitoring device enables the glucose measurements to be collected remotely. For example, the wearable glucose monitoring device may be mailed or otherwise provided to the user, e.g., from the provider of the wearable glucose monitoring device, a pharmacy, a medical testing laboratory, a telemedicine service, and so forth. The user may then wear the wearable glucose monitoring device over the course of the observation period, such as by continuously wearing the device at home or work.

Once obtained, the user can insert a sensor of the wearable glucose monitoring device into the user's body, such as by using an automatic sensor applicator. Unlike the blood draws required by conventional tests such as HbA1c, FPG, and 2 Hr-PG, the user-initiated application of the glucose monitoring device is nearly painless and does not require the withdrawal of blood, consumption of a sugary drink, or fasting. Moreover, the automatic sensor applicator can enable the user to embed the sensor into the user's skin without the assistance of a clinician or healthcare provider. Although an automatic sensor applicator is discussed, the wearable glucose monitoring device may be applied to or otherwise worn by the person in other ways without departing from the spirit or scope of the techniques described herein, such as without the automatic sensor applicator, with assistance of a health care professional (or a health care professional may simply apply the wearable to the person), or by peeling off a protective layer of an adhesive and affixing the adhesive to the person, to name just a few. Once the sensor is inserted into the user's skin, the wearable glucose monitoring device monitors glucose of the person over an observation period of multiple days. It is also to be appreciated that in some implementations, the sensor may not be inserted into the person's skin. Instead, the sensor may simply be disposed against the person's skin in such implementations, like an adhesive patch. Regardless, the sensor of the wearable glucose monitoring device, may continuously detect analytes indicative of the person's glucose and enable generation of glucose measurements.

The glucose measurements collected during the observation period and/or data derived by pre-processing the glucose measurements is provided as input to the trained machine learning model. The trained machine learning model processes the glucose measurements to predict the diabetes classification of the user. Broadly speaking, the diabetes classification describes a state of the user during the observation period, such as having one of diabetes (or a particular type of diabetes such as GDM or Type 2 diabetes), prediabetes (or a particular type of prediabetes such as IFG or IGT), or no diabetes, to name just a few. Notably, unlike conventional tests, the diabetes classification predicted by the machine learning model is based on observed glucose values over multiple days. As such, the prediction is more accurate than tests which rely on a blood sample collected at a single point of time. Moreover, unlike the HbA1c test which is an indirect measurement of blood glucose and can be affected by recent changes in glucose levels caused by external factors or conditions such as sickness or pregnancy, the diabetes classification predicted by the machine learning model is based on glucose measurements directly obtained during a current observation time period.

The diabetes classification prediction is then presented, such as by displaying an indication of the diabetes classification to the user, a doctor, or a guardian of the user via a user interface. Other information may also be presented, such as visualizations of the glucose measurements as well as other statistics derived from the glucose measurements. In some cases, the diabetes classification prediction is presented in a glucose observation report which may also include one or more treatment options for the user, visual representations of the glucose measurements collected by the glucose monitoring device during the observation period, glucose statistics of the user generated based on the collected glucose measurements, levels of severity, next steps (e.g., for a doctor, health care professional, or user), a request to follow-up, a request to order more sensors for the wearable glucose monitoring device, activity levels, trends in glucose or other markers, patterns in the glucose or other markers, patterns in exercise, interpretations of the glucose measurements, or activity related to glycemia. Thus, unlike conventional blood glucose test results, the glucose observation report generated by the one or more machine learning models may include a detailed analysis of the prediction as well as various treatment options. It is to be appreciated that diabetes classifications and information associated with such classifications may be provided in a variety of ways, including, for example, output as an audio signal via a speaker or digital assistant.

Advantageously, utilizing a wearable glucose monitoring device and machine learning to generate predictions which classify people as having a type of diabetes eliminates many of the uncomfortable aspects of the above-noted diagnostic tests and does not limit who can be tested. Unlike HbA1c, for instance, pregnant women can safely wear the wearable glucose monitoring device over the observation period. Moreover, because the machine learning model is applied to glucose traces collected over multiple days, the inconsistencies associated with conventional tests are reduced thereby increasing the accuracy of the prediction as compared to conventional tests based on a single blood sample. By accurately predicting diabetes classifications and notifying users, health care providers, and/or telemedicine services, the described machine learning model allows early detection of diabetes and identifies treatment options which may be taken to mitigate potentially adverse health conditions before the user's diabetes worsens. In so doing, serious damage to the heart, blood vessels, eyes, kidneys, and nerves, and death due to diabetes can be largely avoided.

In the following discussion, an example of an environment is first described that may employ the techniques described herein. Examples of implementation details and procedures are then described which may be performed in the discussed environment as well as other environments. Performance of those procedures is not limited to the example of the environment and the example of the environment is not limited to performance of those procedures.

Example Environment

FIG. 1 is an illustration of an environment 100 in an example of an implementation that is operable to employ diabetes prediction using glucose measurements and machine learning as described herein. The illustrated environment 100 includes person 102, who is depicted wearing a wearable glucose monitoring device 104. The illustrated environment also includes an observation kit provider 106 and an observation analysis platform 108.

In the illustrated example 100, the wearable glucose monitoring device 104 is depicted being provided by the observation kit provider 106 to the person 102, e.g., as part of an observation kit. The wearable glucose monitoring device 104 may be provided as part of an observation kit, for instance, for the purpose of monitoring the person 102's glucose over an observation period lasting multiple days. By way of example, the person 102 may have his or her glucose monitored to predict whether he or she has diabetes (e.g., Type 1 diabetes, Type 2 diabetes, gestational diabetes mellitus (GDM), cystic fibrosis diabetes, and so on) or is at risk for developing diabetes (e.g., prediabetes), and/or whether he or she is predicted to experience adverse effects associated with diabetes (e.g., comorbidity, dysglycemia, macrosomia requiring a cesarean section (C-section), and neonatal hypoglycemia, to name just a few). In connection with the observation period, instructions may be provided to the person 102 that instruct the person 102 to perform one or more activities during the observation period, such as instructing the person 102 to consume a beverage or specific meal (e.g., a same beverage as is consumed in connection with OGTT), avoid one or more specific foods, exercise, and rest, to name just a few. In one or more implementations, the instructions may be provided as part of an observation kit, e.g., written instructions. Alternately or additionally, the observation analysis platform 108 may cause the instructions to be communicated to and output (e.g., for display or audio output) via a computing device associated with the person 102. The observation analysis platform 108 may provide these instructions for output after a predetermined amount of time of an observation period has lapsed (e.g., two days) and/or based on patterns in the glucose measurements obtained. In connection with providing such instructions, the wearable glucose monitoring device 104 automatically monitors the person 102's glucose level after performance of the instructed activity, such as by monitoring an amount the person 102's glucose changes after consuming the meal instructed, performing the exercise instructed, and so forth.

Although discussed throughout as lasting multiple days, in one or more implementations, the observation period may be variable, such that when enough glucose measurements have been collected to accurately predict a diabetes classification for the person 102 the observation period may end. For example, in some cases the person 102's glucose measurements over just a few hours may be processed to predict the person 102 has diabetes with statistical certainty. In this case, the duration of the observation period may be a number of hours rather than multiple days. In general, though, the observation period lasts multiple days to obtain data so that features can be extracted to describe day over day variations in glucose and to prevent erroneous predictions that account for or fail to account for anomalous measurements or observations.

To this end, the observation kit provider 106 may represent one or more of a variety of entities associated with obtaining a prediction regarding whether the person 102 has diabetes or is predicted to experience adverse effects of diabetes. For instance, the observation kit provider 106 may represent a provider of the wearable glucose monitoring devices 104 and of a platform that monitors and analyzes glucose measurements obtained therefrom, such as the observation analysis platform 108 when it also corresponds to the provider of the wearable glucose monitoring device 104. Alternately or additionally, the observation kit provider 106 may correspond to a health care provider (e.g., a primary care physician, OB/GYN, endocrinologist), a doctor's office, a hospital, an insurance provider, a medical testing laboratory, or a telemedicine service, to name just a few. Alternately or additionally, the observation kit provider 106 may correspond to a pharmacist or pharmacy, which may have a physical brick-and-mortar location and/or provide service online. It is to be appreciated that these are just a few examples and the observation kit provider 106 may represent different entities without departing from the spirit or scope of the described techniques.

Given this, provision of the wearable glucose monitoring device 104 to the person 102 may occur in various ways in accordance with the described techniques. For example, the wearable glucose monitoring device 104 may be handed to the person 102 at a doctor's office, hospital, medical testing laboratory, or a brick-and-mortar pharmacy, e.g., as part of an observation kit. Alternately, the wearable glucose monitoring device 104 may be mailed to the person 102, e.g., from the provider of the wearable glucose monitoring device 104, a pharmacy, a medical testing laboratory, a telemedicine service, and so forth. Certainly, the person 102 may obtain the wearable glucose monitoring device 104 for an observation period in other ways in one or more implementations.

Regardless of how the wearable glucose monitoring device 104 is obtained by the person 102, the device is configured to monitor glucose of the person 102 during an observation period, which lasts for a time period spanning multiple days. The wearable glucose monitoring device 104 may be configured with a glucose sensor, for instance, that continuously detects analytes indicative of the person 102's glucose and enables generation of glucose measurements. In the illustrated environment 100 these measurements are represented as glucose measurements 110. In one or more implementations, the wearable glucose monitoring device 104 is a continuous glucose monitoring ("CGM") system. As used herein, the term "continuous" used in connection with glucose monitoring may refer to an ability of a device to produce measurements substantially continuously, such that the device may be configured to produce the glucose measurements 110 at intervals of time (e.g., every hour, every 30 minutes, every 5 minutes, and so forth), responsive to establishing a communicative coupling with a different device (e.g., when a computing device establishes a wireless connection with the wearable glucose monitoring device 104 to retrieve one or more of the measurements), and so forth. The functionality of the wearable glucose monitoring device 104 to produce the glucose measurements 110 along with further aspects of the device's configuration are discussed in more detail in relation to FIG. 2.

Although the wearable glucose monitoring device 104 may be configured in a similar manner as wearable glucose monitoring devices used for treating diabetes, in one or more implementations, the wearable glucose monitoring device 104 may be configured differently than the devices used for treatment. These different configurations may be deployed to control confounding factors of observation periods so that measurements are obtained that accurately reflect the effects of users' normal, day-to-day behavior on their glucose. This can include, for instance, limiting and/or completely preventing users from inspecting those measurements during the observation period. By preventing users from inspecting the glucose measurements 110 over the course of observation periods, the observation configurations further prevent users from seeing or otherwise observing glucose-measurement events (e.g., spikes in glucose) and changing their behavior to counteract such events.

In some cases, the wearable glucose monitoring device 104 may be a specialized device designed specifically for the purpose of collecting glucose measurements for a user during an observation period spanning multiple days so that a diabetes classification may be generated, which may be differentiated in one or more ways from wearable glucose monitoring devices worn by users to treat diabetes. In other instances, such wearable glucose monitoring devices 104 may have the same hardware characteristics as the wearable glucose monitoring devices used to treat diabetes, but may include software that disables or enables different functionality, such as software that prevents the user from inspecting glucose measurements 110 during the observation period. In these instances, functionality that is disabled during the observation period can be enabled after the observation period has ended so that the user has access to the previously-disabled functionality, such as the ability to view glucose measurements in substantially real time.

The different configurations also may be based on differences between how the glucose measurements 110 are used in connection with an observation period for diabetes prediction and how measurements are used in connection with treatment of diabetes. With treatment, continuous or nearly continuous receipt and output of glucose measurements, substantially as those measurements are produced, may be used to inform treatment decisions, e.g., to help a person or his or her caretaker decide what to eat, how to administer insulin, whether to contact a health care provider, and so on. In those scenarios, knowing the measurements and/or trends of the measurements in a timely manner (e.g., substantially real-time) may be critical to effectively mitigating potentially severe adverse effects. By way of contrast, receipt and output of glucose measurements to a person being observed (or a caretaker), as those measurements are being produced, may be unnecessary in connection with diabetes prediction in these scenarios. Instead, the glucose measurements produced for diabetes prediction are handled so that at the end of the observation period, or after some other horizon (e.g., when enough measurements have been produced to achieve statistical certainty), an accurate prediction regarding diabetes can be generated.

Based on such differences with respect to how the glucose measurements are used, the wearable glucose monitoring device 104 may have more local storage than wearable glucose measurement devices used for diabetes treatment, e.g., 10-15 days' worth of glucose-measurement storage for observation configurations versus 3 hours' worth of glucose-measurement storage for treatment configurations. The larger storage capacity of the wearable glucose monitoring device 104 may be suitable to store the glucose measurements 110 for a duration of the observation period. In contrast, wearable glucose measurement devices used for treatment may be configured to offload glucose measurements such that once the measurements are suitably offloaded they are no longer stored locally on those devices. By way of example, wearable glucose devices used for treatment may offload glucose measurements by transmitting them via wireless connections to an external computing device, e.g., at predetermined time intervals and/or responsive to establishing or reestablishing a connection with the computing device.

To the extent that the wearable glucose monitoring device 104 may be configured to store the glucose measurements 110 for an entirety of an observation period, in one or more implementations, the wearable glucose monitoring device 104 may be configured without wireless transmission means, e.g., without any antennae to transmit the glucose measurements 110 wirelessly and without hardware or firmware to generate packets for such wireless transmission. Instead, the wearable glucose monitoring device 104 may be configured with hardware to communicate the glucose measurements 110 via a physical, wired coupling. In such scenarios, the wearable glucose monitoring device 104 may be "plugged in" to extract the glucose measurements 110 from the device's storage.

Accordingly, the wearable glucose monitoring device 104 may be configured with one or more ports to enable wired transmission of the glucose measurements to an external computing device. Examples of such physical couplings may include micro universal serial bus (USB) connections, mini-USB connections, and USB-C connections, to name just a few. Although the wearable glucose monitoring device 104 may be configured for extraction of the glucose measurements 110 via wired connections as discussed just above, in different scenarios, the wearable glucose monitoring device 104 may alternately or additionally be configured to offload the glucose measurements 110 over one or more wireless connections. Implementations involving wired and/or wireless communication of the glucose measurements are discussed further below.

In addition to storage and communication differences, the wearable glucose monitoring device 104 may also include one or more sensors or sensor circuitry configured differently than in devices designed for diabetes treatment. For instance, sensors and the circuitry (e.g., including measurement algorithms) of wearable glucose monitoring devices used for treating diabetes may be optimized for a range of measurements spanning from 40 mg/dL to 400 mg/dL. This is because treatment of diabetes often involves deciding what actions to take to mitigate severe glycemic events that can occur toward ends of the range, e.g., hypo- and hyperglycemia. To predict diabetes, however, fidelity of the measurements over as wide a range may not be needed. Rather, diabetes predictions may be suitably generated in relation to a smaller range, such as a range of glucose measurements spanning from 120 mg/dL to 240 mg/dL. Accordingly, the wearable glucose monitoring device 104 may include one or more sensors or sensor circuitry optimized to produce measurements in such a smaller range. It is to be appreciated that the above-discussed differences are merely examples of how the wearable glucose monitoring device 104 may differ from wearable glucose monitoring devices configured for treatment of diabetes and that the wearable glucose monitoring device 104 may differ from those devices in different ways without departing from the spirit or scope of the described techniques.

Once the wearable glucose monitoring device 104 produces the glucose measurements 110, the measurements are provided to the observation analysis platform 108. As noted above, the glucose measurements 110 may be communicated to the observation analysis platform 108 over wired and/or a wireless connection. In scenarios where the observation analysis platform 108 is implemented partially or entirely on the wearable glucose monitoring device 104, for instance, the glucose measurements 110 may be transferred over a bus from the device's local storage to a processing system of the device. In scenarios where the wearable glucose monitoring device 104 is configured to generate a prediction of a diabetes classification by processing the glucose measurements 110, the wearable glucose monitoring device 104 may also be configured to provide the predicted diabetes classification as output, e.g., by communicating the diabetes classification to an external computing device. In other scenarios, the glucose measurements 110 may be processed by an external computing device configured to predict diabetes classifications.

In one or more implementations, the wearable glucose monitoring device 104 is configured to transmit the glucose measurements 110 to an external device over a wired connection with the external device, e.g., via USB-C or some other physical, communicative coupling. Here, a connector may be plugged into the wearable glucose monitoring device 104 or the wearable glucose monitoring device 104 may be inserted into an apparatus having a receptacle that interfaces with corresponding contacts of the device. The glucose measurements 110 may then be obtained from storage of the wearable glucose monitoring device 104 via this wired connection, e.g., transferred over the wired connection to the external device. Such a connection may be used in scenarios where the wearable glucose monitoring device 104 is mailed by the person 102 after the observation period, such as to a health care provider, telemedicine service, provider of the wearable glucose monitoring device 104, or medical testing laboratory. To this end, an observation kit (not shown) may include packaging (e.g., an envelope or box) to mail the wearable glucose monitoring device 104 to such an entity after observation. Such a connection may also be used in scenarios where the wearable glucose monitoring device 104 is dropped off by the person 102 after the observation period, such as at a doctor's office or hospital (or other establishment of a health care provider), a pharmacy, or a medical testing laboratory. Alternately or additionally, scenarios involving a wired connection may involve the person 102 plugging in the wearable glucose monitoring device 104 to an external computing device after the testing period, e.g., using a cord provided as part of an observation kit. In these scenarios, the external computing device may communicate the glucose measurements 110 to the observation analysis platform 108 over a network (not shown), such as the Internet.

Alternately or additionally, provision of the glucose measurements 110 to the observation analysis platform 108 may involve the wearable glucose monitoring device 104 communicating the glucose measurements 110 over one or more wireless connections. For example, the wearable glucose monitoring device 104 may wirelessly communicate the glucose measurements 110 to external computing devices, such as a mobile phone, tablet device, laptop, smart watch, other wearable health tracker, and so on. Accordingly, the wearable glucose monitoring device 104 may be configured to communicate with external devices using one or more wireless communication protocols or techniques. By way of example, the wearable glucose monitoring device 104 may communicate with external devices using one or more of Bluetooth (e.g., Bluetooth Low Energy links), near-field communication (NFC), Long Term Evolution (LTE) standards such as 5G, and so forth. Wearable glucose monitoring devices 104 may be configured with corresponding antennae and other wireless transmission means in scenarios where the glucose measurements 110 are communicated to an external device for processing. In those scenarios, the glucose measurements 110 may be communicated to the observation analysis platform 108 in various manners, such as at predetermined time intervals (e.g., every day, every hour, or every five minutes), responsive to occurrence of some event (e.g., filling a storage buffer of the wearable glucose monitoring device 104), or responsive to an end of an observation period, to name just a few.

Thus, regardless of where the observation analysis platform 108 is implemented, the observation analysis platform 108 obtains the glucose measurements 110 produced by the wearable glucose monitoring device 104. In one or more implementations, the observation analysis platform 108 may be implemented in whole or in part at the wearable glucose monitoring device 104. Alternately or additionally, the observation analysis platform 108 may be implemented in whole or in part using one or more computing devices external to the wearable glucose monitoring device 104, such as one or more computing devices associated with the person 102 (e.g., a mobile phone, tablet device, laptop, desktop, or smart watch) or one or more computing devices associated with a service provider (e.g., a health care provider, a telemedicine service, a service corresponding to the provider of the wearable glucose monitoring device 104, a medical testing laboratory service, and so forth). In the latter scenario, the observation analysis platform 108 may be implemented at least in part on one or more server devices.

In the illustrated example 100, the observation analysis platform includes storage device 112. In accordance with the described techniques, the storage device 112 is configured to maintain the glucose measurements 110. The storage device 112 may represent one or more databases and also other types of storage capable of storing the glucose measurements 110. The storage device 112 may also store a variety of other data, such as demographic information describing the person 102, information about a health care provider, information about an insurance provider, payment information, prescription information, determined health indicators, account information (e.g., username and password), and so forth. As discussed in more detail below, the storage device 112 may also maintain data of other users of a user population.

In the illustrated example 100, the observation analysis platform 108 also includes prediction system 114. The prediction system 114 represents functionality to process the glucose measurements 110 to generate diabetes predictions, such as to predict whether the person 102 has diabetes (e.g., Type 2 diabetes, GDM, cystic fibrosis diabetes, and so on) or is at risk for developing diabetes (e.g., prediabetes), and/or whether the person 102 is predicted to experience adverse effects associated with diabetes (e.g., comorbidity, dysglycemia, macrosomia requiring a C-section, and neonatal hypoglycemia, to name just a few). As discussed in more detail below, the prediction system 114 uses machine learning to predict diabetes classifications. Use of machine learning may include, for instance, leveraging one or more models generated using machine learning techniques as well as using historical glucose measurements and historical outcome data of a user population.

The illustrated example 100 also includes diabetes classification 116, which may be output by the prediction system 114. In accordance with the described techniques, the diabetes classification 116 may indicate whether it is predicted the person has diabetes or is predicted to experience adverse effects associated with diabetes. The diabetes classification 116 may also be used to generate one or more notifications or user interfaces based on the classification, such as a report directed to a health care provider that includes the diabetes classification (e.g., that the person is predicted to have diabetes) or a notification directed to the person 102 that instructs the person to contact his or her health care provider. Examples of user interfaces that may be generated based on the diabetes classification 116 are described in more detail in relation to FIGS. 6 and 7. In the context of measuring glucose, e.g., continuously, and obtaining data describing such measurements, consider the following discussion of FIG. 2.

Figure 2:
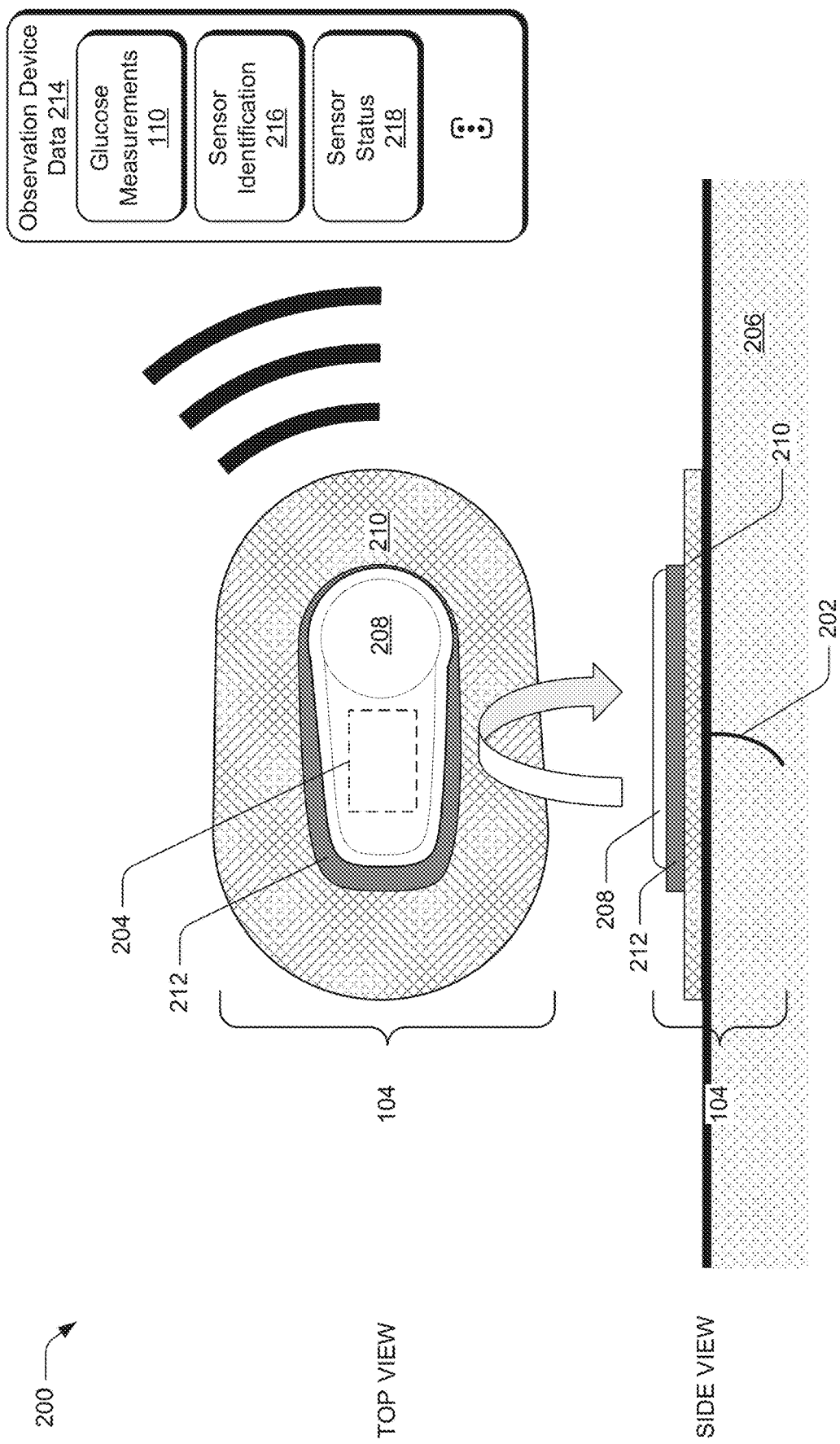
FIG. 2 depicts an example of the wearable glucose monitoring device of FIG. 1 in greater detail.

FIG. 2 depicts an example of an implementation 200 of the wearable glucose monitoring device 104 of FIG. 1 in greater detail. In particular, the illustrated example 200 includes a top view and a corresponding side view of the wearable glucose monitoring device 104. It is to be appreciated that the wearable glucose monitoring device 104 may vary in implementation from the following discussion in one or more of the ways and for one of more of the reasons discussed above in relation to FIG. 1.

In this example 200, the wearable glucose monitoring device 104 is illustrated to include a sensor 202 and a sensor module 204. Here, the sensor 202 is depicted in the side view having been inserted subcutaneously into skin 206, e.g., of the person 102. The sensor module 204 is depicted in the top view as a dashed rectangle. The wearable glucose monitoring device 104 also includes a transmitter 208 in the illustrated example 200. Use of the dashed rectangle for the sensor module 204 indicates that it may be housed or otherwise implemented within a housing of the transmitter 208. In this example 200, the wearable glucose monitoring device 104 further includes adhesive pad 210 and attachment mechanism 212.

In operation, the sensor 202, the adhesive pad 210, and the attachment mechanism 212 may be assembled to form an application assembly, where the application assembly is configured to be applied to the skin 206 so that the sensor 202 is subcutaneously inserted as depicted. In such scenarios, the transmitter 208 may be attached to the assembly after application to the skin 206 via the attachment mechanism 212. Additionally or alternatively, the transmitter 208 may be incorporated as part of the application assembly, such that the sensor 202, the adhesive pad 210, the attachment mechanism 212, and the transmitter 208 (with the sensor module 204) can all be applied at once to the skin 206. In one or more implementations, this application assembly is applied to the skin 206 using a separate sensor applicator (not shown). Unlike the blood draws required by conventional tests such as HbA1c, FPG, and 2 Hr-PG, the user initiated application of the wearable glucose monitoring device 104 is nearly painless and does not require the withdrawal of blood, consumption of a sugary drink, or hours of fasting. Moreover, the automatic sensor applicator enables the person 102 to embed the sensor 202 subcutaneously into the skin 206 without the assistance of a clinician or healthcare provider.

The application assembly may also be removed by peeling the adhesive pad 210 off of the skin 206. It is to be appreciated that the wearable glucose monitoring device 104 and its various components as illustrated are simply one example form factor, and the wearable glucose monitoring device 104 and its components may have different form factors without departing from the spirit or scope of the described techniques.

In operation, the sensor 202 is communicatively coupled to the sensor module 204 via at least one communication channel which can be a wireless connection or a wired connection. Communications from the sensor 202 to the sensor module 204 or from the sensor module 204 to the sensor 202 can be implemented actively or passively and these communications can be continuous (e.g., analog) or discrete (e.g., digital).

The sensor 202 may be a device, a molecule, and/or a chemical which changes or causes a change in response to an event which is at least partially independent of the sensor 202. The sensor module 204 is implemented to receive indications of changes to the sensor 202 or caused by the sensor 202. For example, the sensor 202 can include glucose oxidase which reacts with glucose and oxygen to form hydrogen peroxide that is electrochemically detectable by the sensor module 204 which may include an electrode. In this example, the sensor 202 may be configured as or include a glucose sensor configured to detect analytes in blood or interstitial fluid that are indicative of glucose level using one or more measurement techniques. In one or more implementations, the sensor 202 may also be configured to detect analytes in the blood or the interstitial fluid that are indicative of other markers, such as lactate levels, which may improve accuracy in predicting diabetes classifications. Additionally or alternatively, the wearable glucose monitoring device 202 may include additional sensors to the sensor 202 to detect those analytes indicative of the other markers.

In another example, the sensor 202 (or an additional sensor of the wearable glucose monitoring device 104—not shown) can include a first and second electrical conductor and the sensor module 204 can electrically detect changes in electric potential across the first and second electrical conductor of the sensor 202. In this example, the sensor module 204 and the sensor 202 are configured as a thermocouple such that the changes in electric potential correspond to temperature changes. In some examples, the sensor module 204 and the sensor 202 are configured to detect a single analyte, e.g., glucose. In other examples, the sensor module 204 and the sensor 202 are configured to detect multiple analytes, e.g., sodium, potassium, carbon dioxide, and glucose. Alternately or additionally, the wearable glucose monitoring device 104 includes multiple sensors to detect not only one or more analytes (e.g., sodium, potassium, carbon dioxide, glucose, and insulin) but also one or more environmental conditions (e.g., temperature). Thus, the sensor module 204 and the sensor 202 (as well as any additional sensors) may detect the presence of one or more analytes, the absence of one or more analytes, and/or changes in one or more environmental conditions.

In one or more implementations, the sensor module 204 may include a processor and memory (not shown). The sensor module 204, by leveraging the processor, may generate the glucose measurements 110 based on the communications with the sensor 202 that are indicative of the above-discussed changes. Based on these communications from the sensor 202, the sensor module 204 is further configured to generate observation device data 214. The observation device data 214 is a communicable package of data that includes at least one glucose measurement 110. Alternately or additionally, the observation device data 214 includes other data, such as multiple glucose measurements 110, sensor identification 216, sensor status 218, and so forth. In one or more implementations, the observation device data 214 may include other information such as one or more of temperatures that correspond to the glucose measurements 110 and measurements of other analytes. It is to be appreciated that the observation device data 214 may include a variety of data in addition to at least one glucose measurement 110 without departing from the spirit or scope of the described techniques.

In implementations where the wearable glucose monitoring device 104 is configured for wireless transmission, the transmitter 208 may transmit the observation device data 214 wirelessly as a stream of data to a computing device. Alternately or additionally, the sensor module 204 may buffer the observation device data 214 (e.g., in memory of the sensor module 204) and cause the transmitter 208 to transmit the buffered observation device data 214 later at various intervals, e.g., time intervals (every second, every thirty seconds, every minute, every five minutes, every hour, and so on), storage intervals (when the buffered observation device data 214 reaches a threshold amount of data or a number of instances of observation device data 214), and so forth.

With respect to the observation device data 214, the sensor identification 216 represents information that uniquely identifies the sensor 202 from other sensors, such as other sensors of other wearable glucose monitoring devices 104, other sensors implanted previously or subsequently in the skin 206, and so on. By uniquely identifying the sensor 202, the sensor identification 216 may also be used to identify other aspects about the sensor 202 such as a manufacturing lot of the sensor 202, packaging details of the sensor 202, shipping details of the sensor 202, and so on. In this way, various issues detected for sensors manufactured, packaged, and/or shipped in a similar manner as the sensor 202 may be identified and used in different ways, e.g., to calibrate the glucose measurements 110, to notify users of defective sensors, to notify manufacturing facilities of machining issues, and so forth.

The sensor status 218 represents a state of the sensor 202 at a given time, e.g., a state of the sensor at a same time one of the glucose measurements 110 is produced. To this end, the sensor status 218 may include an entry for each of the glucose measurements 110, such that there is a one-to-one relationship between the glucose measurements 110 and statuses captured in the sensor status 218 information. Generally speaking, the sensor status 218 describes an operational state of the sensor 202. In one or more implementations, the sensor module 204 may identify one of a number of predetermined operational states for a given glucose measurement 110. The identified operational state may be based on the communications from the sensor 202 and/or characteristics of those communications.

By way of example, the sensor module 204 may include (e.g., in memory or other storage) a lookup table having the predetermined number of operational states and bases for selecting one state from another. For instance, the predetermined states may include a "normal" operation state where the basis for selecting this state may be that the communications from the sensor 202 fall within thresholds indicative of normal operation, e.g., within a threshold of an expected time, within a threshold of expected signal strength, an environmental temperature is within a threshold of suitable temperatures to continue operation as expected, and so forth. The predetermined states may also include operational states that indicate one or more characteristics of the sensor 202's communications are outside of normal activity and may result in potential errors in the glucose measurements 110.

For example, bases for these non-normal operational states may include receiving the communications from the sensor 202 outside of a threshold expected time, detecting a signal strength of the sensor 202 outside a threshold of expected signal strength, detecting an environmental temperature outside of suitable temperatures to continue operation as expected, detecting that the person 102 has rolled (e.g., in bed) onto the wearable glucose monitoring device 104, and so forth. The sensor status 218 may indicate a variety of aspects about the sensor 202 and the wearable glucose monitoring device 104 without departing from the spirit or scope of the described techniques.

Having considered an example of an environment and an example of a wearable glucose monitoring device, consider now a discussion of some examples of details of the techniques for diabetes prediction using glucose measurements and machine learning in a digital medium environment in accordance with one or more implementations.

Diabetes Prediction

Figure 3:
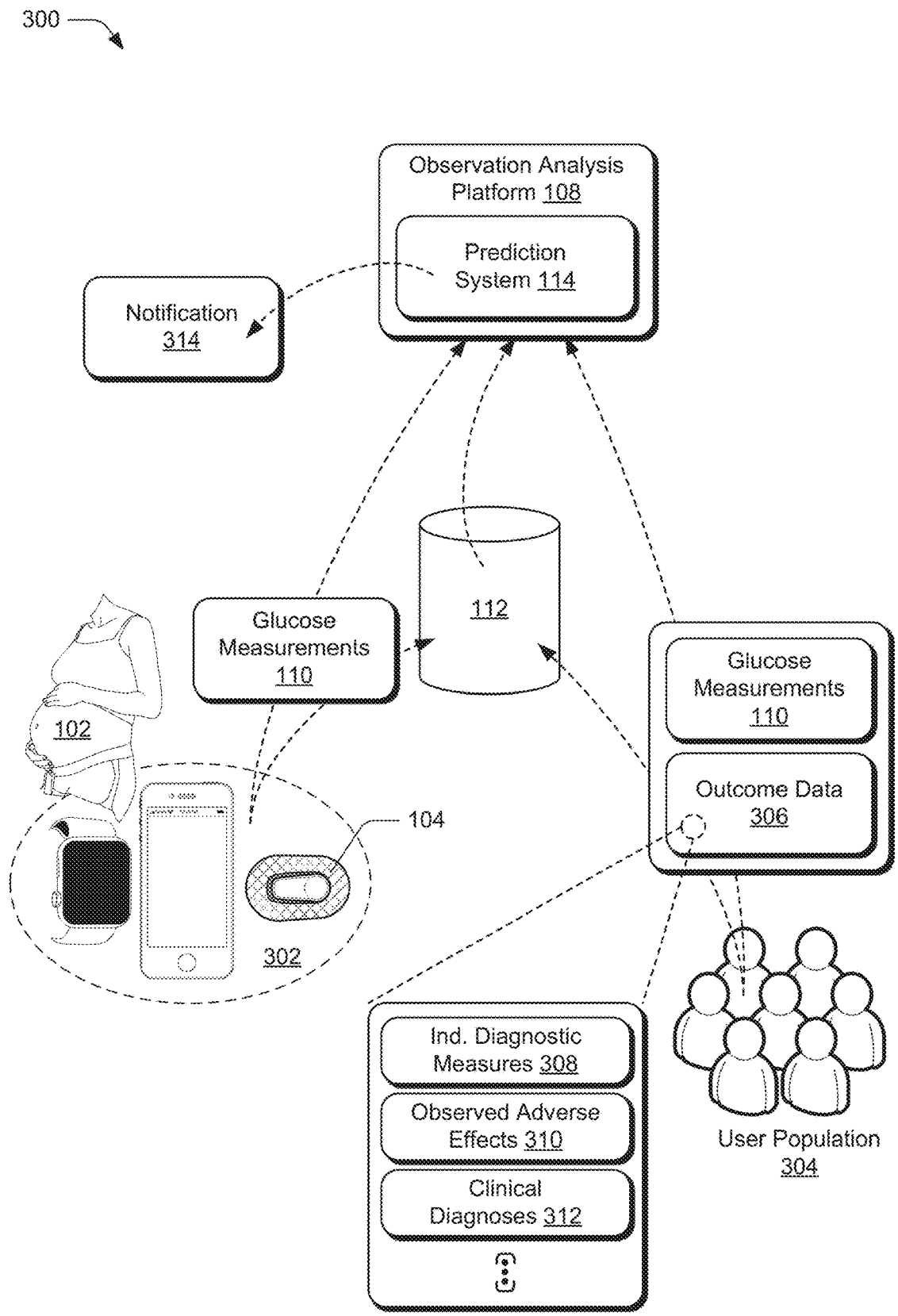
FIG. 3 depicts an example of an implementation in which diabetes-related data, including glucose measurements, is routed to different systems in connection with diabetes prediction.

FIG. 3 depicts an example of an implementation 300 in which diabetes-related data, including glucose measurements, is routed to different systems in connection with diabetes prediction.

The illustrated example 300 includes from FIG. 1 the observation analysis platform 108 and the person 102. The illustrated example 300 also depicts devices 302 associated with the person 102 that may provide the glucose measurements 110 to the observation analysis platform 108 and/or the storage device 112 in connection with diabetes prediction. The devices 302 depicted include the wearable glucose monitoring device 104, worn by the person 102 during the observation period to produce the glucose measurements 110, along with additional devices external to the wearable glucose monitoring device 104. Specifically, the additional, external devices depicted include a mobile phone and a smart watch, although various other devices may be configured to provide the glucose measurements 110 to the observation analysis platform 108 and/or the storage device 112 in one or more implementations, e.g., laptops, tablet devices, wearable health trackers, and so on.

As mentioned above, the glucose measurements 110 may be communicated or otherwise provided via wired or wireless connections to the observation analysis platform 108 and/or the storage device 112. For example, the wearable glucose monitoring device 104 may provide the glucose measurements 110 to the observation analysis platform 108 and/or the storage device 112 via a wired or wireless connection as discussed above. In scenarios where one of the additional, external devices 302 provides the glucose measurements 110, the glucose measurements 110 may first be provided from the wearable glucose monitoring device 104 to the additional, external device, such that the additional, external device communicates or otherwise provides the glucose measurements 110 to the observation analysis platform 108 and/or the storage device 112.

In these scenarios, the additional, external devices 302 may act as an intermediary between the wearable glucose monitoring device 104 and the observation analysis platform 108 and the storage device 112, such that the external devices 302 are used to "route" the glucose measurements 110 from the wearable glucose monitoring device 104 to the observation analysis platform 108 and/or the storage device 112. Alternately or additionally, other devices may route the glucose measurements 110 from the wearable glucose monitoring device 104 to the observation analysis platform 108 and/or the storage device 112. Those other devices may include dedicated devices that are configured to extract the data from the wearable glucose monitoring device 104 and that are associated with an entity involved in the diabetes prediction, such as a health care provider, hospital, pharmacy, telemedicine service, medical testing laboratory, and so on.

The illustrated example 300 also includes user population 304. The user population 304 represents multiple users that correspond to persons that have worn glucose monitoring devices, such as the wearable glucose monitoring device 104. It follows then that the glucose measurements 110 of these other users are provided by their respective monitoring devices and/or by external computing devices to the observation analysis platform 108 and/or the storage device 112. In one or more implementations, the user population 304 includes users selected as part of one or more "studies" conducted, at least in part, for the purpose of collecting data (including the glucose measurements 110) so that the data can be used to generate one or more models using machine learning, e.g., using supervised learning, unsupervised learning, reinforcement learning, and so forth.

Alternately or in addition, the user population 304 may include users for which a diabetes prediction was previously generated based on his or her glucose measurements produced during an observation period involving the wearable glucose monitoring device 104—in a similar manner as the diabetes prediction is generated for the person 102. Data that is produced prior to the diabetes prediction for the person 102 and in connection with studies carried out to collect the data is referred to as "historical" data because it is produced at a point in time before the person 102's glucose measurements 110 are produced. Similarly, data produced prior to the diabetes prediction of the person 102 and in connection with diabetes predictions of other users is also historical data. In accordance with the described techniques, the historical data includes, for example, historical glucose measurements and historical outcome data. This historical data is used along with machine learning to train or otherwise learn an underlying model as described in more detail in relation to FIG. 5.

By way of example, studies to collect data in connection with diabetes prediction may involve participants wearing a glucose monitoring device over a time period of multiple days to produce the glucose measurements 110 for those participants. The time period may have a same or different duration from the observation period used to produce the person 102's glucose measurements 110 without departing from the spirit or scope of the described techniques. In addition to collecting the glucose measurements 110, such studies may be leveraged to obtain other data about the participants. Outcome data 306 corresponds to at least some of this other data and may describe a variety of aspects about users of the user population 304.

In connection with a study, for example, participants may, in addition to wearing glucose monitoring devices, be tested using conventional techniques that produce one or more diagnostic measures, such as HbA1c, FPG, and/or 2 Hr-PG. Independent diagnostic measures 308 represents data describing outcomes of one or more such tests in relation to the users of the user population 304. For example, the independent diagnostic measures 308 may describe results of HbA1c, FPG, 2 Hr-PG (or OGTT as a combination of FPG and 2 Hr-PG), and/or random plasma glucose (RPG) in relation to the users of the user population 304. Given this, the glucose measurements 110 of a study participant may be associated with the respective participant's independent diagnostic measures 308, e.g., by labeling the measurements. As discussed in more detail below, machine learning may, through a training process, learn patterns in the glucose measurements 110 that are indicative of particular values of the independent diagnostic measures 308, such as patterns in the glucose measurements 110 that indicate a respective person's HbA1c is likely 10.0.

As illustrated, the outcome data 306 also includes observed adverse effects 310 and clinical diagnoses 312. The observed adverse effects 310 represents data describing adverse effects experienced by users of the user population 304. By way of example, the observed adverse effects 310 may describe whether a user has or has not experienced any of one or more adverse effects associated with Type 2 diabetes, such as diabetic retinopathy, cataracts, glaucoma, blindness, severe hyper- or hypo-glycemia, heart and blood vessel disease, neuropathy, erectile dysfunction, kidney failure or end-stage kidney disease, slow healing, hearing impairment, skin conditions (e.g., bacterial and fungal infections), sleep apnea, and Alzheimer's disease, to name just a few.

Additionally or alternatively, the observed adverse effects 310 may describe whether a user has or has not experienced any of one or more adverse effects associated with GDM, such as her baby having excessive birth weight (requiring a C-section birth), an early (preterm) birth, her baby having respiratory distress syndrome, neonatal hypoglycemia, her baby becoming obese or developing Type 2 diabetes later in life, still birth, and so on.

Additionally or alternatively, the observed adverse effects 310 may describe whether a user has or has not experienced one or more adverse effects associated with other types of diabetes, such as effects associated with Type 1 diabetes, cystic fibrosis diabetes, pancreatic diabetes, and so on. Given this, the glucose measurements 110 of a study participant may be associated with the respective participant's observed adverse effects 310, e.g., by labeling the measurements. As discussed in more detail below, machine learning may, through a training process, learn patterns in the glucose measurements 110 that are indicative of occurrence and non-occurrence of the observed adverse effects 310, such as patterns in glucose measurements 110 that indicate a probability of a respective person having a baby with excessive birth weight requiring a C-section.

The clinical diagnoses 312 represents data describing whether users of the user population 304 have been diagnosed (or not) with diabetes by a clinician or whether they have been provisionally or preliminarily diagnosed with diabetes. By way of example, the diagnoses may be made by a clinician based on one or more of the independent diagnostic measures 308 and/or the observed adverse effects 310. Additionally or alternatively, the clinical diagnoses 312 may be configured to represent labeling based on diagnostic tests that are not approved for diagnosis by, for example, the Food and Drug Administration (FDA) or the clinical community at large, such as A1CNOW+. The values of the clinical diagnoses 312 may represent that a respective user is clinically diagnosed with diabetes (or some type of diabetes), is clinically diagnosed with prediabetes (or any of the different types of prediabetes), is provisionally or preliminarily diagnosed with diabetes, does not have diabetes (i.e., screened), is diagnosed with diabetes using a non-approved test, or is diagnosed with prediabetes using a non-approved test, to name just a few. Given this and the independent diagnostic measures 308, for instance, the glucose measurements 110 may be associated with a respective study participant's independent diagnostic measures 308 and the respective participant's clinical diagnosis 312. The machine learning may, through training, learn patterns in the glucose measurements 110 that are indicative of particular values of the independent diagnostic measures 308 and further are indicative of different diabetes diagnoses, such as patterns in glucose measurements 110 that indicate a person's HbA1c is likely 6.0 (e.g., "estimated A1c") and further that a clinician's analysis likely results in a diagnosis of prediabetes. Although this example is discussed in relation to the person's HbA1c, it is to be appreciated that a clinical diagnosis may be made based on different measurements (e.g. FPG) and/or observations (e.g., weight gain, neuropathy, and sleep apnea) without departing from the spirit or scope of the described techniques.

In one or more implementations, the outcome data 306 may include or be usable as labels. For example, a value of an independent diagnostic measure 308 may be used to label the glucose measurements 110 of a respective user of the user population 304. Alternately or in addition, labels indicative of observed adverse effects 310 experienced by the respective user may be used to label the glucose measurements 110 of the respective user. Alternately or in addition, labels indicative of a clinical diagnosis 312 may be used to label the glucose measurements 110 of the respective user, e.g., the glucose measurements 110 of a user clinically diagnosed with prediabetes may be associated with a 'prediabetes' label whereas the glucose measurements 110 of a different user clinically diagnosed with diabetes may be associated with a 'diabetes' label. Although the independent diagnostic measures 308, the observed adverse effects 310, and the clinical diagnoses 312 are depicted in the example 300, it is to be appreciated that the outcome data 306 may include data describing different, additional, or fewer aspects of users of the user population 304 without departing from the spirit or scope of the described techniques.

As depicted in the illustrated example 300, the glucose measurements 110 and the outcome data 306 of users of the user population 304 is communicated or otherwise provided to the observation analysis platform 108 and/or the storage device 112. In addition to the glucose measurements 110 and the outcome data 306, additional data describing other aspects of users of the user population 306 may be obtained by the observation analysis platform 108 and/or the storage device 112. By way of example, this additional data may include demographic data (e.g., age, gender, ethnicity), medical history data (e.g., height, weight, body mass index (BMI), body fat percentage, presence or absence of various conditions), stress data, nutrition data, exercise data, prescription data, height and weight data, occupation data, and so forth. These types of additional data are merely examples and the additional data may include more, fewer, or different types of data without departing from the spirit or scope of the techniques described herein. In one or more implementations, the observation analysis platform 108 and/or the storage device 112 may obtain such additional data (or at least some of the additional data) about the person 102 as well as about the users of the user population 304.

Notably, the illustrated example 300 depicts the observation analysis platform 108 and the storage device 112 separately and also depicts a dashed arrow between the storage device 112 and the observation analysis platform 108. Generally speaking, this arrow represents that the data maintained in the storage device 112 may be obtained by the observation analysis platform 108 from the storage device 112. Said another way, the data maintained by the storage device 112 may be provided to the observation analysis platform 108. As discussed above, the storage device 112 may store the glucose measurements 110 of the person 102 as well as the glucose measurements 110 and the outcome data 306 of the user population 304.

In one or more implementations, the observation analysis platform 108 and the storage device 112 may correspond to a same entity, such as a provider of glucose monitoring devices (e.g., the wearable glucose monitoring device 104) and services related to glucose monitoring. In such implementations, the observation analysis platform 108 and the storage device 112 may be implemented in the "cloud," across multiple computing devices (e.g., servers) and storage resources allocated to or otherwise associated with the entity (e.g., via a subscription or ownership). To this end, the glucose measurements 110 of the person 102 as well as the glucose measurements 110 and the outcome data 306 of the user population 304 may be obtained by the observation analysis platform 108 from the storage device 112 in ways that a server associated with a service provider obtains data from storage associated with that service provider.

In other implementations, the observation analysis platform 108 and the storage device 112 may correspond to different entities. By way of example, the storage device 112 may correspond to a first entity, such as a computing device (e.g., mobile phone or tablet device) of the person 102, and the observation analysis platform 108 may correspond to a second entity, such as a provider of glucose monitoring devices and services related to glucose monitoring. In this example, the observation analysis platform 108 may implemented, at least in part, as an application of the second entity, running on the person 102's computing device. Alternately or additionally, the observation analysis platform 108 may be implemented using a server device of the second entity. In the application implementation, the second entity's application may obtain one or more of the glucose measurements 110 of the person 102, the glucose measurements 110 of the user population 304, or the outcome data of the user population 304 from the storage device 112 implemented locally on the computing device, e.g., over a bus or other local transmission means of the computing device. In the server implementation, the server of the second entity may obtain data from the storage device 112, implemented on the computing device, over one or more networks, such as the Internet.

In another example where the observation analysis platform 108 and the storage device 112 correspond to different entities, the storage device 112 may correspond to a first entity, such as a provider of the glucose monitoring devices and services related to glucose monitoring (or limited services related to glucose monitoring). In this latter example, the observation analysis platform 108 may correspond to a second, different entity, such as a service provider, e.g., a data partner of the first entity. In this example, the second entity may be considered a "third party" in relation to the entity corresponding to the storage device 112 (and the wearable glucose monitoring device 104). When it corresponds to a data partner, the observation analysis platform 108 may obtain data from the first entity (i.e., the storage device 112) in accordance with one or more legal agreements between the first and second entities. Provision of the data maintained in the storage device 112 to the observation analysis platform 108 may be controlled by an application programming interface (API).

In this type of scenario, such an API may be considered an "egress" for data, such as the glucose measurements 110 and the outcome data 306. By "egress" it is meant that a flow of data is generally outward from the first entity to a third party (e.g., the second entity). In the context of data provision, an API may expose one or more "calls" (e.g., specific formats for data requests) to the third party. By way of example, an API may expose those calls to the third party after the third party enters into an agreement, e.g., with a business corresponding to the first entity, that allows the third party to obtain data from the storage device 112 via the API. As part of this agreement, the third party may agree to exchange payment in order to obtain data from the first entity. Alternately or additionally, the third party may agree to exchange data that it produces, e.g., via an associated device, in order to obtain data from the first entity. Parties that enter into agreements to obtain data (e.g., the glucose measurements 110) from the first entity via an API may be referred to as "data partners." In operation, the API allows the third party to make a request for data (e.g., glucose measurements 110 and/or the outcome data 306) maintained in the storage device 112 in a specific request format, and if the request is made in the specific format, then the first entity provides the requested data in a specific response format. The requested data may be provided in the specific response format in one or more communications (e.g., packets) over a network, e.g., the Internet. Examples of a second entity that may be considered a "third party" include various service providers, such as service providers that provide one or more health monitoring/tracking services, fitness related services, telemedicine services, medical testing laboratory services, and so forth. Indeed, the storage device 112 and the observation analysis platform 108 may be implemented using a variety of devices and/or resources (e.g., computing, communication, storage, etc.), and divisions (or not) between the entities, corresponding to the various devices and/or resources, may differ from those described above without departing from the spirit or scope of the techniques described herein.

Regardless, the observation analysis platform 108 is configured to obtain the glucose measurements 110 of the person 102 as well as the glucose measurements 110 and the outcome data 306 of the user population 304 and to process them in accordance with the described techniques. Using the glucose measurements 110 and the outcome data 306 of the user population 304, for example, the prediction system 114 is configured to generate one or more machine learning models, e.g., regression models, neural networks, reinforcement learning agents. Once one or more such models are generated, the prediction system 114 is configured to use those one or more models to process the glucose measurements of the person 102 to predict the diabetes classification 116 for the person 102.

In the illustrated example 300, the prediction system 114 is shown outputting notification 314. The notification 314 may be based on the diabetes classification 116 or include the diabetes classification 116. Consider an example in which the diabetes classification 116 output by the prediction system 114's one or more machine learning models is a label that indicates the person 102 is predicted to have diabetes, e.g., a '1' (where a '0' indicates no diabetes) or a text label such as 'diabetes'. In this case, simply providing the diabetes classification 116 to the person 102 may be undesirable. When such information is not delivered with pertinent educational material or is not delivered in an appropriate setting and in a personalized manner, provision of such information may affect the person 102 in a variety of negative ways, such as by causing confusion, anger, depression, and so on. Accordingly, the notification 314 may simply be based on the diabetes classification 116, such as by notifying the person 102 that the results of the observation period are available and instructing them to schedule an appointment with his or her associated health care provider.

By way of contrast, providing the diabetes classification 116 to a health care provider of the person 102 may not be undesirable. Instead, providing the diabetes classification 116 to the health care provider may be preferred (in contrast to not providing the classification) so that the health care provider can suitably inform the person 102 and also develop a treatment plan for the person 102. In such scenarios, the notification 314 may simply correspond to the diabetes classification 116. Alternately, notifications communicated to health care providers (or others) may be configured as reports that include the diabetes classification 116 along with other information, such as traces of the person 102's glucose measurements 110 over the observation period, measures derived from those glucose measurements 110, recommendations for treatment (e.g., learned from historical data of the user population 304), and so forth. Examples of these notifications are discussed in more detail in relation to FIGS. 6 and 7. In the context of predicting a glucose classification 116 for the person 102 from the person 102's glucose measurements 110, consider the following discussion of FIG. 4.

Figure 4:
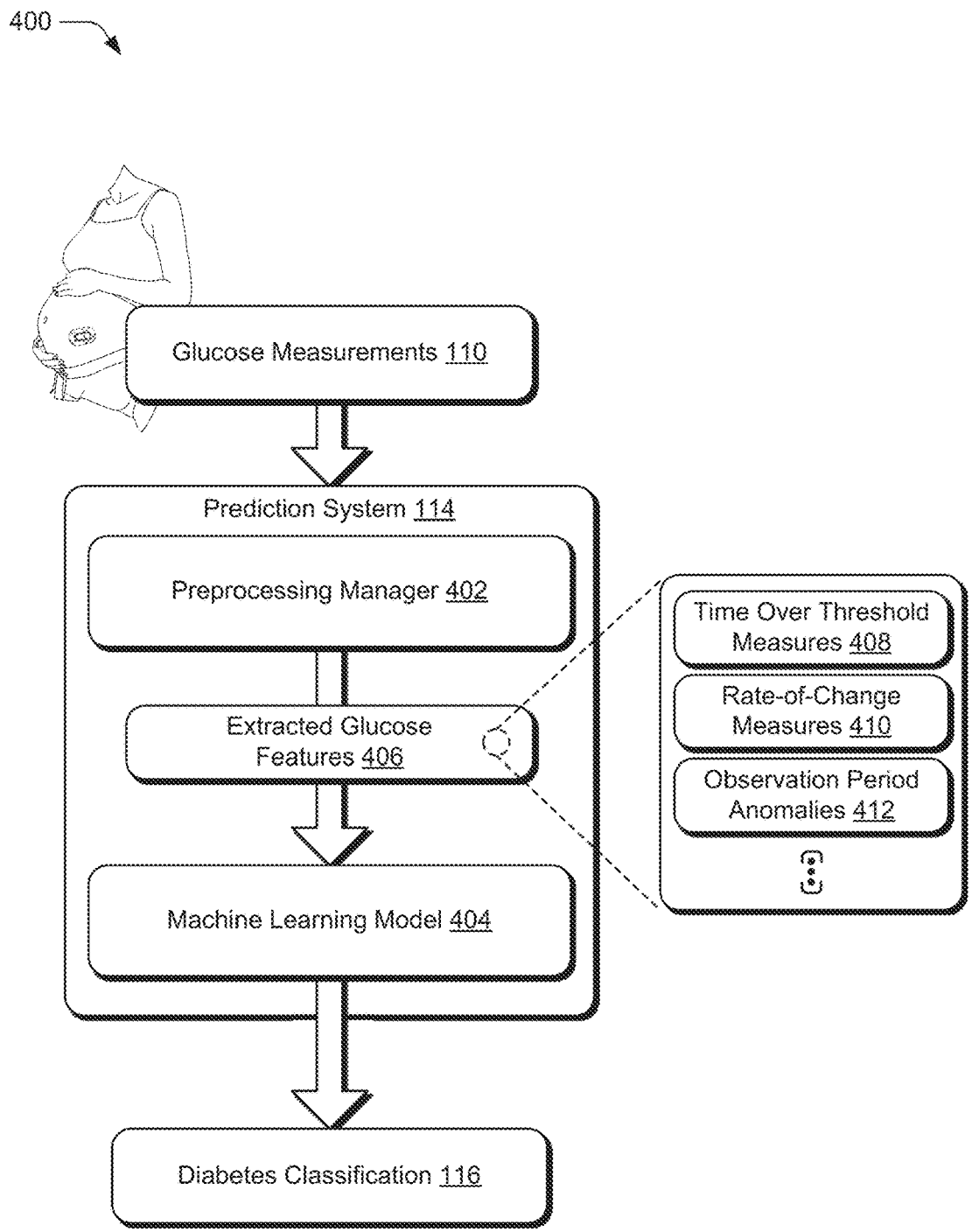
FIG. 4 depicts an example of an implementation of the prediction system of FIG. 1 in greater detail in which a diabetes classification is predicted using machine learning.

FIG. 4 depicts an example of an implementation 400 of the prediction system of FIG. 1 in greater detail in which a diabetes classification is predicted using machine learning.

In the illustrated example 400, the prediction system 114 is shown obtaining the glucose measurements 110, e.g., from the storage device 112. Here, the glucose measurements 110 correspond to the person 102. In this example 400, the prediction system 114 is depicted including preprocessing manager 402 and machine learning model 404, which are configured to generate a prediction of the diabetes classification 116 based on the glucose measurements 110 of the person 102. Although the prediction system 114 is depicted including these two components, it is to be appreciated that the prediction system 114 may have more, fewer, and/or different components to generate the diabetes classification 116 based on the glucose measurements 110 without departing from the spirit or scope of the described techniques.

In one or more implementations, the glucose measurements 110 are configured as time-sequenced data, such that each of the glucose measurements 110 corresponds to a timestamp. For example, the glucose measurements 110 may be configured as one or more glucose "traces." Although the glucose measurements 110 may generally be received or maintained in order, e.g., by the observation analysis platform 108 from the wearable glucose monitoring device 104 and/or an external device, in some instances, one or more of the glucose measurements 110 may not be received or maintained in a same order as the glucose measurements 110 are produced. For instance, packets with the glucose measurements 110 may be received out of order. Thus, the order of receipt may not chronologically match the order in which the glucose measurements 110 are produced by the wearable glucose monitoring device 104. In addition or alternately, transmissions including one or more of the glucose measurements 110 may be corrupted. Indeed, there may be a variety of reasons why the glucose measurements 110, as obtained by the prediction system 114, are not entirely in time order.

To this end, the preprocessing manager 402 may be configured to determine a time-ordered sequence of the glucose measurements 110 according to respective timestamps. Due to corruption and communication errors, the glucose measurements 110 obtained by the prediction system 114 may not only be out of time order but may also be missing one or more measurements—there may be gaps in the time-ordered sequence where one or more measurements are expected. In these instances, the preprocessing manager 402 may be further configured to interpolate the missing glucose measurements and incorporate them into the time-ordered sequence. Although this functionality is discussed, in one or more implementations, the glucose measurements 110 as obtained by the prediction system 114 may already be in time order (e.g., one or more time-series of the glucose measurements 110), such that ordering those measurements and interpolating missing measurements is not performed by the preprocessing manager 402.

In general, the preprocessing manager 402 is configured to preprocess the glucose measurements 110 to generate data (e.g., one or more feature vectors) that can be provided as input to the machine learning model 404 and data that can be reported in connection with the diabetes classification 116 (e.g., included as part of the notification 314). In the illustrated example 400, the preprocessing manager 402 is depicted outputting extracted glucose features 406. The preprocessing manager 402 may determine the extracted glucose features 406 by processing the glucose measurements 110 according to one or more predetermined algorithms or functions. Each of the different extracted glucose features 406 may correspond to a different algorithm or function with which the preprocessing manager 402 processes the glucose measurements 110.

Here, the extracted glucose features 406 include time over threshold measures 408, rate-of-change measures 410, and observation period anomalies 412. It is to be appreciated that the extracted glucose features 406 may vary from the combination illustrated without departing from the spirit or scope of the described technique. For example, the extracted glucose features 406 may also or alternately include one or more of mean glucose (e.g., over the duration of the observation period or daily), median glucose, inter quartile range of the glucose measurements 110, variance of the glucose measurements 110, nocturnal hyperglycemia, differences between average glucose during waking hours and average glucose during sleeping hours, day-to-day variability of glucose, day-to-night variability of glucose, statistical distributions of glucose, threshold percentile of glucose (e.g., statistically significant threshold percentile such as $94^{th}$ percentile or greater), 10 to 90 percentile range of glucose, standard deviation of glucose, mean of daily difference (MODD), and mean amplitude of glycemia excursions (MAGE), to name just a few.

Notably, the time over threshold measures 408 and the rate-of-change measures 410 are measures that simply cannot be determined using conventional diagnostic tests. Instead, the time over threshold measures 408 and the rate-of-change measures 410 are necessarily time based, requiring that the data points (i.e., the glucose measurements 110) each be associated with a point in time and sequenced according to their times. Generally, the time over threshold measures 408 correspond to an amount of time during the observation period that the glucose measurements 110 of the person 102 are above a glucose threshold. To compute the time over thresholds measures 408, for instance, the preprocessing manager 402 may identify sequentially consecutive glucose measurements 110 over a glucose threshold (e.g., based on a comparison of the measurements to the threshold) and determine a difference in time between a first of those measurements over the threshold and a last of the measurements over the threshold. In the absence of times associated with each of the measurements and absent producing the measurements at increments of time that are suitably granular to capture such features, determining an amount of time over a glucose threshold simply is not possible. It is to be appreciated that an amount of time over a threshold contrasts with a number of measurements over a threshold or percentage of measurements over a threshold, which the preprocessing manager 402 may also be configured to determine.

Generally, the rate-of-change measures 410 correspond to a difference in glucose measurements 110 of the user over a unit of time. To determine the rate-of-change measures 410, the preprocessing manager 402 may determine, between at least two measurements, a difference in the measured amount of glucose and a difference in time, such that a change in amount of glucose over some unit of time may be determined, e.g., mg/dL change per minute. It is to be appreciated that such rates of change may be determined using more than two of the glucose measurements 110. Regardless, without time sequencing of the glucose measurements 110, the rate-of-change measures 410 simply cannot be determined. These rate-of-change measures 410 may indicate how quickly the person 102's body reacts when his or her glucose spikes as a result of eating carbohydrates—this may further be indicative of the person 102's insulin response. Summarily, the time-sequencing of the glucose measurements 110 enables a variety of measures to be determined that cannot be determined using the data from other diagnostic tests.

Examples of the time over threshold measures 408 may include, by way of example and not limitation, time over 130 mg/dL (which corresponds to an amount of time during the course of the observation period where the person 102's glucose level is over 130 mg/dL) and time over 140 mg/dL (which corresponds to an amount of time during the course of the observation period where the person 102's glucose level is over 140 mg/dL). In one or more implementations, a time over threshold measure 408 may correspond to an amount of time over a threshold which may range from 120 mg/dL to 240 mg/dL. Further, the time over threshold measures 408 may include just a single time over threshold measure, such as time over 140 mg/dL, or multiple measures, such as an amount of time over 130 mg/dL, an amount of time over 140 mg/dL, and an amount of time over 150 mg/dL.

Other time-based threshold measures that the preprocessing manager 402 may determine as part of or in addition to the extracted glucose features 406 include a time within range measure, which corresponds to an amount of time during the course of the observation period that the person 102's glucose is between a first glucose level and a second glucose level that is less than the first glucose level, corresponding to upper and lower limits of a range, respectively. Conversely, the preprocessing manager 402 may determine a time outside range measure, which corresponds to an amount of time over the course of the observation period the person 102's glucose measurements 110 are outside such a range. Examples of the rate-of-change measures 410 may include, for instance, average rate-of-change after a glucose high measure, average rate-of-change after carbohydrate consumption measure, rate-of-change over times of day (e.g., at night), and so on.

The preprocessing manager 402 may determine the observation period anomalies 412 using any of a variety of known statistical anomaly detection techniques, including, for example, unsupervised anomaly detection techniques, supervised anomaly detection techniques, and semi-supervised anomaly detection techniques. Additionally, the preprocessing manager 402 may determine one or more statistical measures in relation to time of day, such as nighttime mean and median glucose measurements. Again, such measures cannot be determined without the glucose measurements 110 having corresponding times.

In addition to determining these different features of the glucose, the preprocessing manager 402 may determine which of the glucose measurements 110 are to serve as a basis for input to the machine learning model 404. In other words, the preprocessing manager 402 may filter the glucose measurements 110 by removing at least a portion of the glucose measurements 110 from being input into the machine learning model 404. The preprocessing manager 402 may then determine the extracted glucose features 406 from the filtered glucose measurements.

By way of example, the preprocessing manager 402 may select a subset of the measurements (e.g., measurements from the three "worst" days) of the glucose measurements 110, generate the extracted glucose features 406 for the subset of measurements, and then generate input data for input to the machine learning model 404 based on the extracted glucose features 406 of the subset of measurements. Alternately, the preprocessing manager may select a subset of the days, where x-number of the worst days are removed (or unselected for inclusion in the subset). Regardless, the unselected measurements and/or data corresponding to the unselected measurements may not be input to the machine learning model 404, in one or more implementations. The preprocessing manager 402 may select which of the glucose measurements 110 are to serve as a basis for the input data in a variety of ways, such as based on daily means of the glucose measurements (e.g., where the worst days are the days with the highest mean glucose, such as the three days with the highest mean glucose), based on performance of the wearable glucose monitoring device 104 (e.g., first and last days may be eliminated or days may be eliminated due to receipt of device or sensor errors), and so on. In addition to data removal, the preprocessing manager 402 may alternately or additionally replace or add one or more of the glucose measurements 110 with higher-fidelity measurements, such as measurements interpolated during the preprocessing.

Regardless of the particular glucose features extracted, the preprocessing manager 402 is configured to generate input data for input to the machine learning model 404. In one or more implementations, this input data may be configured as a feature vector that represents one or more features. In one example, the input data may correspond to a single feature, such as a time over threshold measure 408, e.g., time over 140 mg/dL. In this example, the preprocessing manager 402 may generate a feature vector that represents the amount of time the person 102's glucose was over the threshold during the observation period (or percentage of time). In other examples, the input data may correspond to multiple features, such as a time over threshold measure 408 and a mean glucose. Accordingly, the preprocessing manager 402 may generate a feature vector that represents both the amount of time the person 102's glucose was over the threshold during the observation period (or percentage of time) as well as the person 102's mean glucose during the observation period. It is to be appreciated that any of the above discussed extracted glucose features 406 (or other determinations) may be used in single-feature implementations and that any combination of those features (or determinations) may be used in multi-feature implementations.

In addition to features extracted from the glucose measurements 110, the preprocessing manager 402 may also incorporate features from additional data, describing different aspects of the person 102. As mentioned above, this additional data may include additional analyte data (e.g., lactate measurements), environmental data (e.g., the person's temperature), already-observed adverse effects data (e.g., data describing that any of a variety of adverse effects associated with diabetes have already been observed), demographic data (e.g., describing age, gender, ethnicity) collected through a questionnaire or otherwise obtained, medical history data, stress data, nutrition data, exercise data, prescription data, height and weight data, occupation data, and so forth. In other words, the data provided as input to the machine learning model 404 or an ensemble of the machine learning models 404 may, in one or more implementations, describe a variety of aspects about the person 102 (e.g., as features of input feature vectors) in addition to glucose-based features without departing from the spirit or scope of the described techniques. In such scenarios, the machine learning model 404 is trained using similar historical data of the user population 304.

Although the illustrated example 400 depicts the preprocessing manager 402 preprocessing the glucose measurements 110 to produce the extracted glucose features 406, and using those features as input to the machine learning model (e.g., feature vectors indicative of extracted features), in one or more implementations, the preprocessing manager 402 may generate feature vectors that represent (alone or with other features) one or more time-series of the glucose measurements 110 (e.g., traces). Thus, the input data to the machine learning model 404 may correspond to, or otherwise include, a vectorized time-series of the glucose measurements 110 or multiple vectorized time-series of the glucose measurements 110. In implementations where time series glucose measurements are vectorized, the machine learning model 404 may, for example, correspond to a neural network. In implementations where extracted glucose features 406 such as time over threshold measures 408 and statistical features (e.g., inter quartile range) are vectorized, the machine learning model may, for example, correspond to a regression model, e.g., a linear or logistic regression model.

Responsive to receiving the input data from the preprocessing manager 402, the machine learning model 404 is configured to generate and output the diabetes classification 116. Specifically, the machine learning model 404 may be trained to output the diabetes classification 116. By way of example, the machine learning model 404 may be trained, or an underlying representation may be learned, based on one or more training approaches and using historical glucose measurements and outcome data from which diabetes classifications can be derived, such as using the glucose measurements 110 and the outcome data 306 of the user population 304. In accordance with the described techniques, the machine learning model 404 may represent one or more models, including, for instance, a model trained to predict whether the person has diabetes and, in one or more implementations, an additional model to predict whether the person does not have diabetes (i.e., a diabetes classification that can be used to screen the person as not having diabetes with a degree of certainty). Each of the models of a multi-model configuration may receive differently configured input data that describes different aspects, e.g., feature vectors with features that represent different aspects related to diabetes. It is to be appreciated that in other implementations, a single model may be configured to generate both types of predictions. In one or more implementations, the machine learning model 404 may be configured as an ensemble of models that each generates a different prediction related to diabetes than the other models.

The diabetes classification 116 may classify the person 102 in terms of one or more outcomes, which correspond to the outcomes described by the outcome data 306 used to train the machine learning model 404. In implementations where the machine learning model 404 is trained, or the model is learned, using the clinical diagnoses 312 of the user population 304, then the machine learning model 404 may classify the person 102's glucose measurements 110 into a class corresponding to one of the diagnoses, e.g., diabetes, prediabetes, or no diabetes. To this end, a health care provider may use the diabetes classification 116 to treat the person 102 or develop a treatment plan similarly to how the health care provider 102 would do so if diagnosed with diabetes according to conventional techniques, e.g., HbA1c, FPG, and/or 2 Hr-PG.

Similarly, where the machine learning model is trained, or the model is learned, using the observed adverse effects 310 of the user population, then the machine learning model 404 may output probabilities that the person 102's glucose measurements 110 are indicative of the person experiencing the different adverse effects, e.g., a probability from zero to one that the person will experience any of the variety of adverse effects associated with different types of diabetes. In some implementations, there may be a machine learning model trained or built for each effect, such that the machine learning model 404 represents an ensemble of models capable of generating predictions regarding whether the person 102 will or will not experience each effect—or a probability of the person to experience each effect.

In implementations where the machine learning model is trained, or the model is learned, using the independent diagnostic measures 308 of the user population, then the machine learning model 404 may output a prediction of a value of a particular diagnostic measure, e.g., an HbA1c value, a FPG value, a 2 Hr-PG value, or an OGTT value. The diabetes classification 116 that is output depends largely on how the machine learning model 404 is trained and the information, specifically, the diabetes classification 116 represents—such as a label indicative of whether or not the person has diabetes or is at risk for having diabetes (e.g., a diabetes label, a prediabetes label, or a no-diabetes label), a label indicative of whether or not the person has a particular type of diabetes (e.g., Type 1 diabetes, Type 2 diabetes, and GDM), a probability, or a measure value—depends on the training. Additionally, different types of machine learning models may be better suited to generate predictions in relation to different types of outcomes that can be represented by the diabetes classification 116. In the context of training the machine learning mode, consider now the following discussion of FIG. 5.

Figure 5:
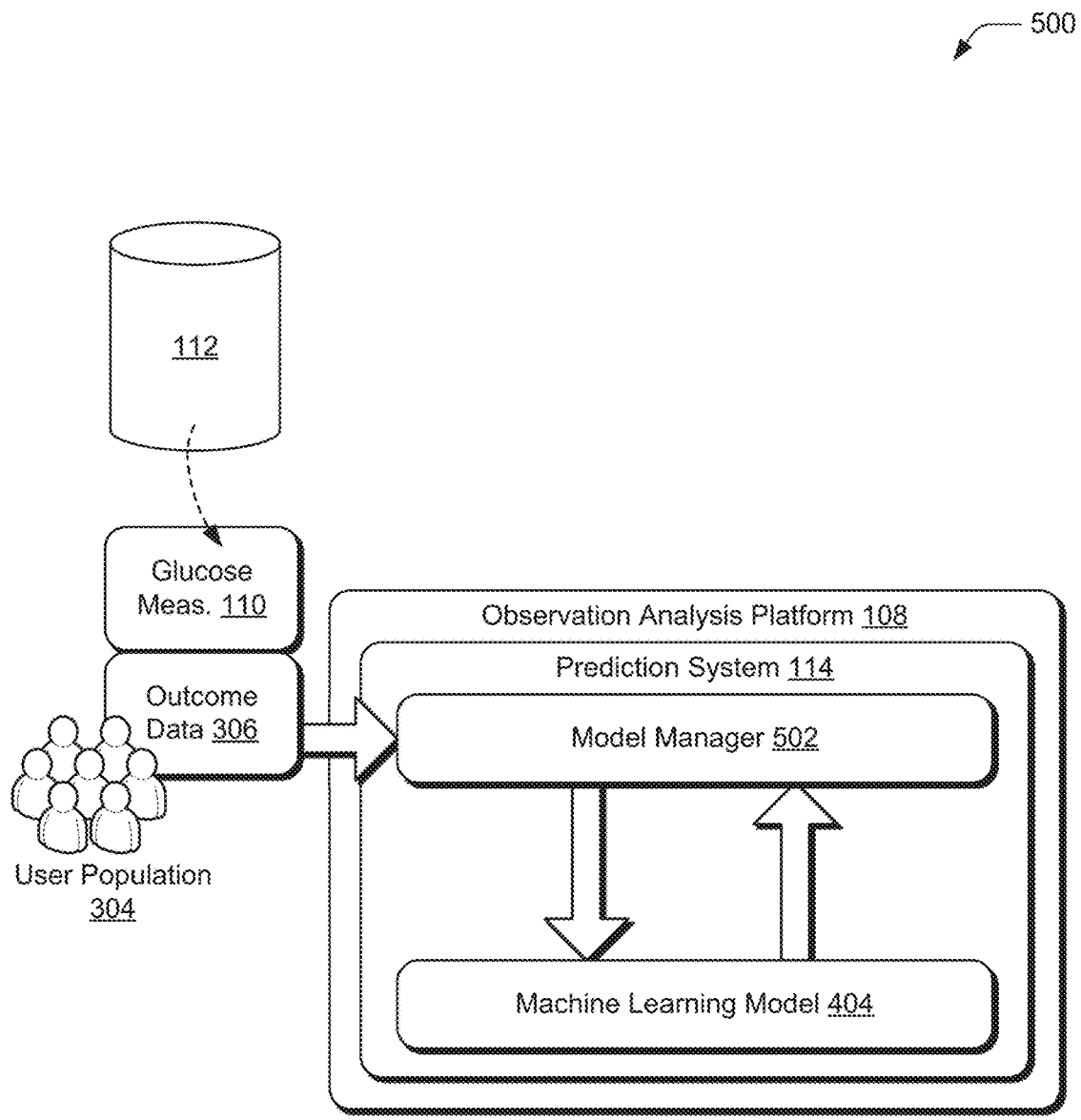
FIG. 5 depicts an example of an implementation of the prediction system of FIG. 1 in greater detail in which a machine learning model is trained to predict diabetes classifications.

FIG. 5 depicts an example of an implementation 500 of the prediction system 114 in greater detail in which a machine learning model is trained to predict diabetes classifications.

In the illustrated example 500, the prediction system 114 includes model manager 502, which manages the machine learning model 404. In accordance with the described techniques, the machine learning model 404 may represent a single machine learning model or an ensemble of multiple models. The machine learning model 404 may correspond to different types of machine learning models, where the underlying models are learned using different approaches, such as using supervised learning, unsupervised learning, and/or reinforcement learning. By way of example, these models may include regression models (e.g., linear, polynomial, and/or logistic regression models), classifiers, neural networks, and reinforcement learning based models, to name just a few.

The machine learning model 404 may be configured as, or include, other types of models without departing from the spirit or scope of the described techniques. These different machine learning models may be built or trained (or the model otherwise learned), respectively, using different data and different algorithms due, at least in part, to different architectures and/or learning paradigms. Accordingly, it is to be appreciated that the following discussion of the model manager 502's functionality is applicable to a variety of machine learning models. For explanatory purposes, however, the functionality of the model manager 502 will be described generally in relation to a statistical model and a neural network.

Broadly speaking, the model manager 502 is configured to manage machine learning models, including the machine learning model 404. This model management includes, for example, building the machine learning model 404, training the machine learning model 404, updating this model, and so forth. Specifically, the model manager 502 is configured to carry out this model management using, at least in part, the wealth of data maintained in the storage device 112. As illustrated, this data includes the glucose measurements 110 and the outcome data 306 of the user population 304. Said another way, the model manager 502 builds the machine learning model 404, trains the machine learning model 404 (or otherwise learns the underlying model), and updates this model using the glucose measurements 110 and the outcome data 306 of the user population 304. In implementations where the machine learning model 404 receives data in addition to the glucose measurements or the extracted features of those measurements as input, the model manager 502 also uses such additional data of the user population 304 to build, train, and update the machine learning model 404.

In one or more implementations, the model manager 502 generates training data to train the machine learning model 404 or to otherwise learn parameters of the model. Broadly speaking, generation of the training data is dependent on the diabetes classification the machine learning model is designed to output. This training data will be different, for instance, if the machine learning model 404 is configured to generate predictions of diagnostic measures of a person, adverse effects the person is predicted to experience, or clinical diagnoses of the person. Regardless of the outcome to be predicted, generating the training data may include time sequencing the glucose measurements 110 of the user population 304 (if the glucose measurements 110 are not already time-sequenced) and extracting glucose features from those time-sequenced glucose measurements 110. The model manager 502 may leverage the functionality of the preprocessing manager 402 to form time sequenced glucose measurements 110 and to extract glucose features, for instance, in a similar manner as discussed above in relation to generating the extracted glucose features 406.

Generating the training data also includes associating the traces of the glucose measurements 110 or features extracted from the glucose measurements 110 (e.g., similar to the extracted glucose features but for the glucose measurements 110 the user population 304) with the outcome data 306 of a respective user of the user population 304. Given this, a glucose trace or an extracted glucose feature corresponding to a particular user is associated with outcome data 306 of the particular user. By way of example, a particular user may have been clinically diagnosed with diabetes and his or her glucose may have been above a threshold for an amount of time corresponding to 27% of an observation period. Given this, the model manager 502 may form a training instance that includes an input portion with a value indicating the user's time above threshold is 27% and having an associated output portion with a value indicating the person has diabetes, e.g., '1' or some other corresponding value.

In one or more implementations, the model manager 502 may build a statistical model by extracting from the outcome data 306 observed values or labels corresponding to at least one type of outcome, such as values of the clinical diagnoses 312, e.g., 'diabetes', 'prediabetes', and 'no diabetes' or values indicative of those labels. Once built, the statistical model is configured to predict values or labels of this at least one outcome type and output them as the diabetes classification 116—values or labels indicative of the at least one outcome type do not serve as input to the model. In scenarios where the statistical model is a regression model, for instance, outcome values or labels may correspond to one or more dependent variables. In contrast, one or more of the glucose features extracted from the glucose measurements 110 may serve as input to the model. Thus, in scenarios where the machine learning model 404 is configured as a statistical model, the one or more glucose features may correspond to one or more explanatory (or independent) variables.

Given the set of outcome values or labels from the outcome data 306 and the set of values of features extracted from the glucose measurements 110, the model manager 502 uses one or more known approaches for "fitting" these sets of values to an equation so that it produces the outcome values or labels responsive to input of the extracted glucose feature values, within some tolerance. Examples of such fitting approaches include using a least squares approach, using a least absolute deviations regression, minimizing a penalized version of the least squares cost function (e.g., ridge regression or lasso), and so forth. By "fitting" it is meant that the model manager 502 estimates model parameters for the equation using the one or more approaches and these sets of values of the training data.

The estimated parameters include, for instance, weights to apply to values of the independent variables (e.g., the extracted glucose features 406) when they are input to the machine learning model during operation. The model manager 502 incorporates these parameters estimated from fitting the observed values of the user population 304 into the equation to generate the machine learning model 404 as a statistical model. In operation, the prediction system 114 inputs values of the independent variables (e.g., values of one or more of the extracted glucose features 406) into the statistical model (e.g., as one or more vectors or a matrix), the statistical model applies the estimated weights to these input values, and then outputs values or labels for the one or more dependent variables. This output corresponds to the diabetes classification 116.

In the following discussion, the capabilities of the model manager 502 to build and train machine learning models is discussed in relation to a configuration of the machine learning model 404 corresponding to or including at least one neural network.

With respect to the training data used, the model manager 502 may, as noted above, generate instances of the training data including an input portion and an expected output portion, i.e., a ground truth for comparison to the model's output during training. The input portion of a training data instance may correspond to one or more traces of glucose measurements 110 and/or one or more extracted features of the glucose measurements 110 of a particular user. The output portion may correspond to one or more values of the particular user's outcome data 306, e.g., a value indicative of a clinical diagnosis of diabetes or a value of the user's observed HbA1c. Again, whether traces are used for training as well as which extracted features are used for training and which outcome data is used for training depends on the data the machine learning model 404 is designed (and trained) to receive as input and the data it is designed (and trained) to output.

The model manager 502 uses the training input portions along with the respective expected output portions to train the machine learning model 404. In the context of training, the model manager 502 may train the machine learning model 404 by providing an instance of data from the set of training input portions to the machine learning model 404. Responsive to this, the machine learning model 404 generates a prediction of a diabetes classification, such as by predicting a value indicative of a clinical diagnosis of diabetes or a value of the user's observed HbA1c. The model manager 502 obtains this training prediction from the machine learning model 404 as output and compares the training prediction to the expected output portion that corresponds to the training input portion. For example, if the machine learning model 404 outputs a diabetes classification indicating that the user has diabetes, then this prediction is compared to the output data (e.g., which classifies the user as having diabetes or no diabetes) to determine if the prediction was correct. Based on this comparison, the model manager adjusts internal weights of the machine learning model 404 so that the machine learning model can substantially reproduce the expected output portion when the respective training input portion is provided as input in the future.

This process of inputting instances of the training input portions into the machine learning model 404, receiving training predictions from the machine learning model 404, comparing the training predictions to the expected output portions (observed) that correspond to the input instances (e.g., using a loss function such as mean squared error), and adjusting internal weights of the machine learning model 404 based on these comparisons, can be repeated for hundreds, thousands, or even millions of iterations—using an instance of training data per iteration.

The model manager 502 may perform such iterations until the machine learning model 404 is able to generate predictions that consistently and substantially match the expected output portions. The capability of a machine learning model to consistently generate predictions that substantially match expected output portions may be referred to as "convergence." Given this, it may be said that the model manger 502 trains the machine learning model 404 until it "converges" on a solution, e.g., the internal weights of the model have been suitably adjusted due to training iterations so that the model consistently generates predictions that substantially match the expected output portions.

As noted above, the machine learning model 404 may be configured to receive input in addition to traces of glucose measurements and/or features extracted from those measurements in one or more implementations. In such implementations, the model manager 502 may form training instances that include the training input portion, the respective expected output portion and also additional input data describing any other aspects of the user population 304 being used to predict diabetes classifications, e.g., demographic information, medical history, exercise, and/or stress. This additional data as well as the training input portion may be processed by the model manger 502 according to one or more known techniques to produce an input vector. This input vector, describing the training input portion as well as the other aspects, may then be provided to the machine learning model 404. In response, the machine learning model 404 may generate a prediction of diabetes classification in a similar manner as discussed above, such that the prediction can be compared to the expected output portion of the training instance and weights of the model adjusted based on the comparison.

Once the machine learning model 404 is trained, it is used to predict diabetes classifications as discussed above and below. As also noted, the diabetes classifications output by the machine learning model 404 may serve as a basis for a variety of information provided to the person 102 in relation to which the prediction is generated as well as others associated with the person, such as the person 102's health care provider, a caregiver, a telemedicine or health tracking service, and so forth. In the context of information that may be output based on the predictions, consider the following discussion of FIGS. 6-8.

Figure 6:
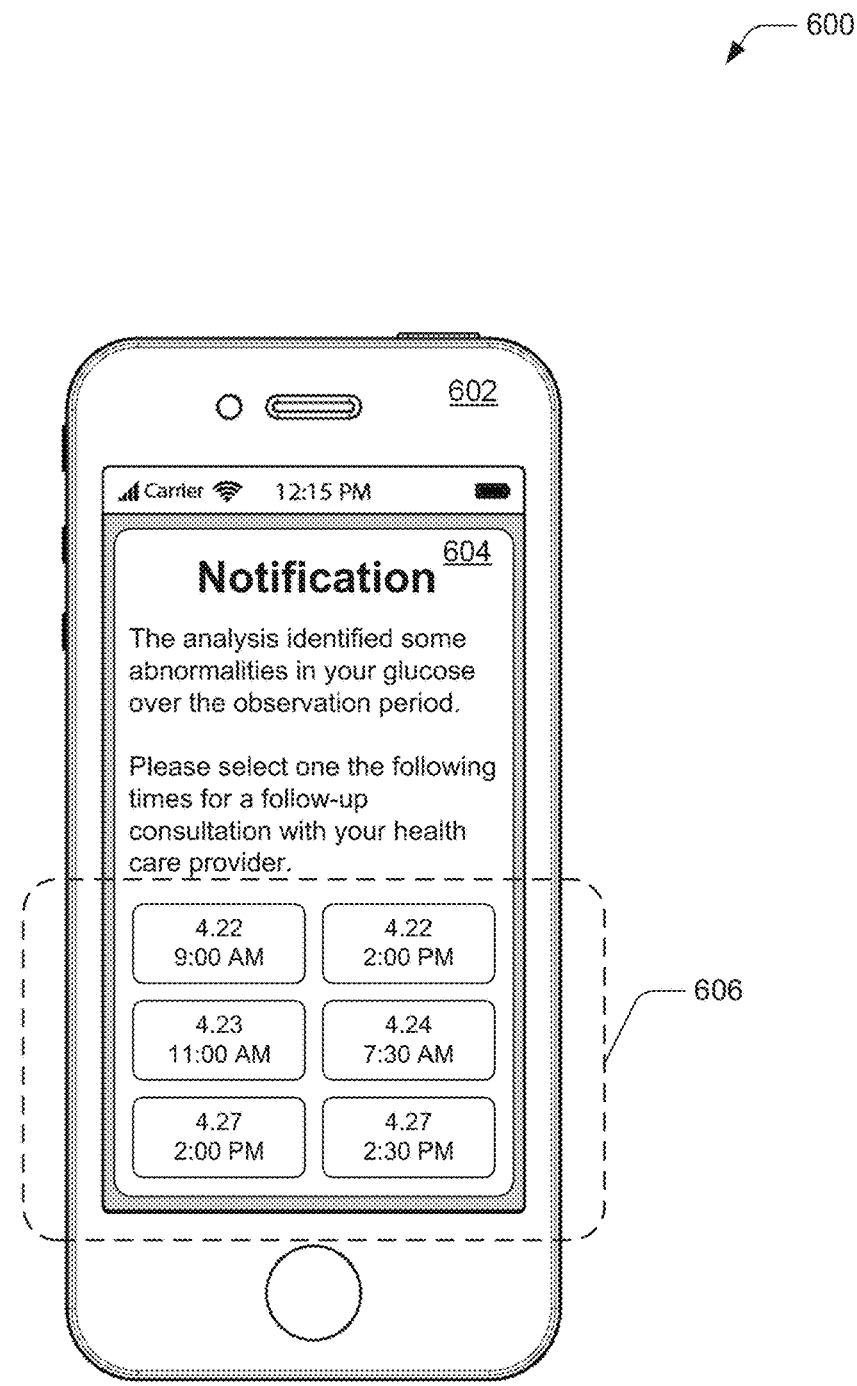
FIG. 6 depicts an example of an implementation of a user interface displayed for notifying a user about a diabetes prediction that is generated based on glucose measurements collected during an observation period.

FIG. 6 depicts an example of an implementation 600 of a user interface displayed for notifying a user about a diabetes prediction generated based on glucose measurements produced during an observation period.

The illustrated example 600 includes computing device 602 displaying user interface 604. In this example 600, the user interface 604 may correspond to the notification 314. This example 600 represents a scenario where the notification 314 (i.e., the user interface 604) is generated based on the diabetes classification 116 but does not include the diabetes classification 116. Here, the computing device 602 may be associated with the person 102 whose glucose measurements are collected during the observation period and in relation to which the diabetes classification 116 is generated (or the computing device 604 may be associated with another person associated with the person 102 such as a caregiver).

To this end, the user interface 604 may be displayed to notify the person 102 (or an associated person) about the diabetes classification 116 without revealing the predicted classification. This is because output of the diabetes classification 116 to the actual person 102 the classification corresponds to may affect the person 102 in a variety of negative ways, such as by causing confusion, anger, depression, and so on. In this example 600, the user interface 604 includes a summary about the processing of the person 102's glucose measurements. The user interface 604 also includes a recommendation of actionable behavior based on the diabetes classification—in this case recommending that the person 102 follow up with his or her health care provider. In addition, the user interface 604 includes graphical user interface elements 606 that are selectable to carry out the recommended behavior. Each of the user interface elements 606 may be selectable to cause a follow up appointment with a health care provider of the person 102 to be scheduled, such as an appointment at a physical location of the health care provider or an appointment via a telephone or video conference, e.g., in connection with remote health care and/or a telemedicine service. It is to be appreciated that notifications based on the diabetes classification 116, but that do not include the classification may be configured in different ways without departing from the spirit or scope of the described techniques.

Figure 7:
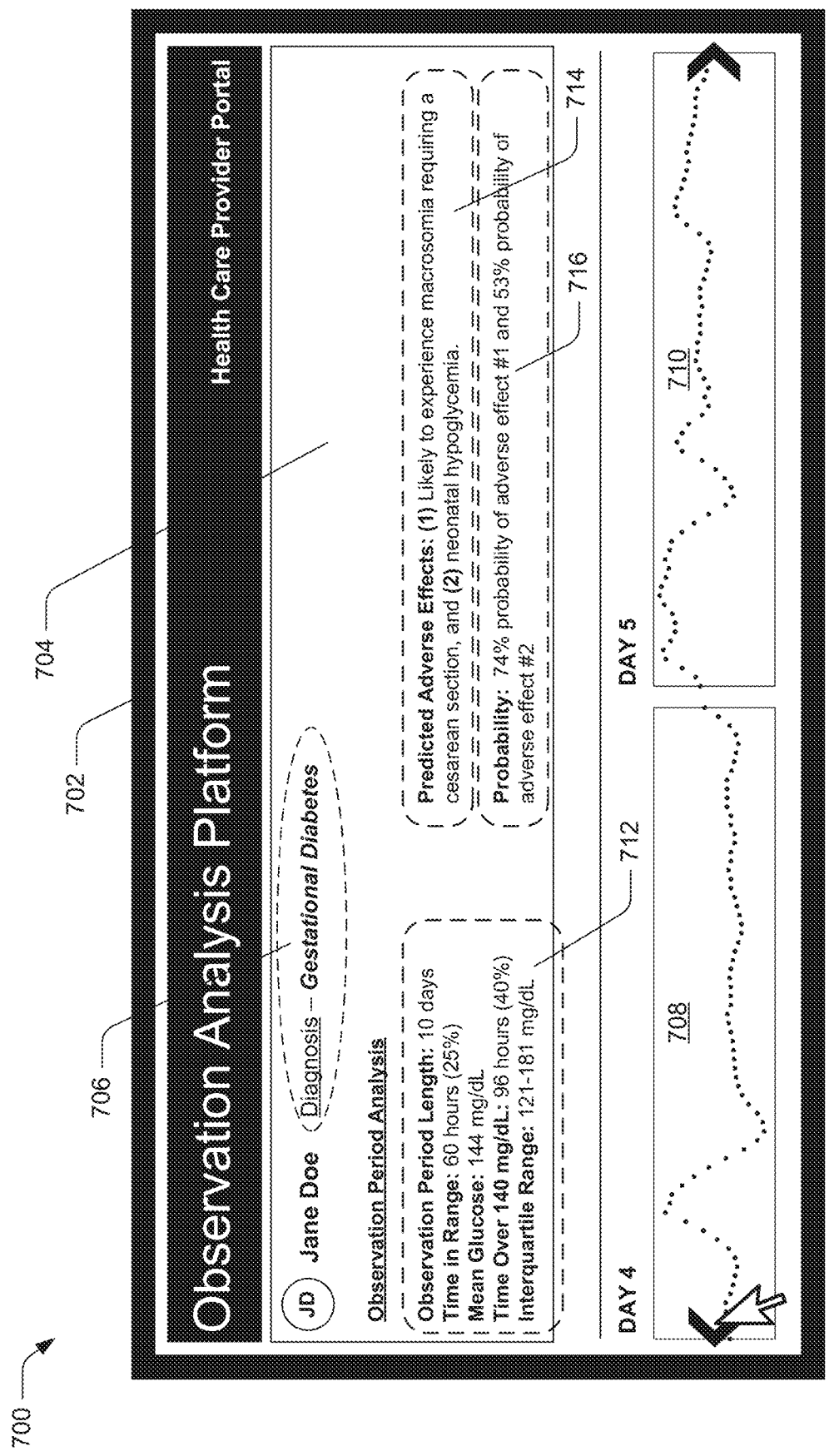
FIG. 7 depicts an example of an implementation of a user interface displayed for reporting a diabetes prediction of a user along with other information produced in connection with the diabetes prediction.

FIG. 7 depicts an example of an implementation 700 of a user interface displayed for reporting a diabetes prediction of a user along with other information produced in connection with the diabetes prediction.

The illustrated example 700 includes display device 702 displaying user interface 704 configured as a report. In this example, the user interface 704 may correspond to the notification 314. In contrast to the example depicted in FIG. 6, this example 700 represents a scenario where the notification includes the diabetes classification 116. In this illustrated example 700, graphical diagnosis element 706 represents or otherwise indicates the diabetes classification 116. Here, the display device 702 may be associated with a health care provider associated with the person 102 whose glucose measurements are collected during the observation period and in relation to which the diabetes classification 116 is generated.

To this end, the user interface 704 may be displayed to report the diabetes classification 116 to the health care provider and to report additional information that may be pertinent to the classification. In operation, a health care provider may independently analyze the additional information reported and provide a different diagnosis from the one indicated by the diabetes classification 116. In this example 700, the additional information includes glucose traces 708, 710. Those traces represent two days' worth of the person 102's glucose measurements 110 collected over the observation period. The user interface 704 is also depicted with controls that may allow a user to navigate to other glucose measurements 110 collected, such as traces corresponding to previous or subsequent days of the observation period.

The user interface 704 also includes graphical glucose feature elements 712, which represent or otherwise indicate one or more of the extracted glucose features 406 determined by the preprocessing manager 402 based on the person 102's glucose measurements 110. In addition to a predicted clinical diagnosis, as indicated by the graphical diagnosis element 706, the user interface 704 also includes predicted adverse effects elements 714 and probability elements 716. The inclusion of these elements represents that the machine learning model 404 may be configured (e.g., via configuration as an ensemble of models and/or based on architecture and training) to generate predictions of more than one type of diabetes classification. By way of example, the machine learning model 404 may be configured to predict a clinical diagnosis of the person 102, values for one or more of a plurality of independent diagnostic measures (e.g. HbA1c, FPG, 2 Hr-PG, and OGTT), and probabilities that the person 102 will experience one or more of a plurality of adverse effects of diabetes.

In particular, the predicted adverse effects elements 714 correspond to adverse effects the diabetes classification indicates the person 102 is more likely to experience than not, e.g., based on a probability output by the machine learning models of experiencing those effects being greater than 50%. It is to be appreciated that adverse effects for which the machine learning model 404 predicts any probability at all of occurring may also be output in one or more scenarios along with the corresponding probabilities. The probability elements 716 include the probabilities that the adverse effects indicated by the elements 714 will occur. The probabilities indicated by these probability elements 716 may be output by the machine learning model 404 in one or more implementations. It is to be appreciated that reports that include the diabetes classification 116 may be configured in different ways without departing from the spirit or scope of the described techniques, such as a document suitable for printing.

Figure 8:
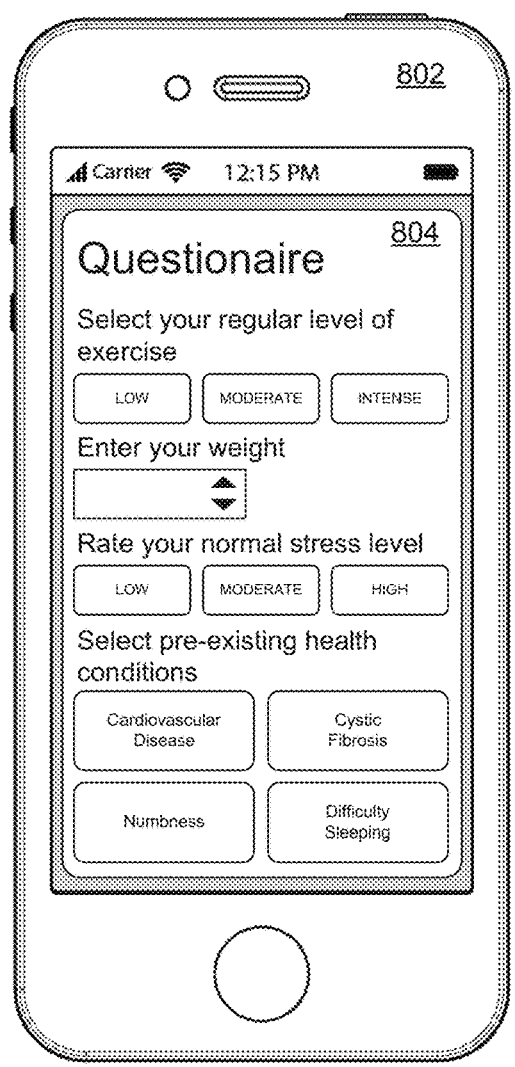
FIG. 8 depicts an example of an implementation of a user interface displayed for collecting additional data that can be used as input to machine learning models for generating a diabetes prediction.

FIG. 8 depicts an example of an implementation 800 of a user interface displayed for collecting additional data that can be used as input to machine learning models for generating a diabetes prediction.

The illustrated example 800 includes computing device 802 displaying user interface 804. In this example 800, the user interface 804 may be displayed to collect data about the person 102 in addition to the glucose measurements 110 collected during the observation period. This additional data, along with traces of the glucose measurements 110 and/or one or more of the extracted glucose features 406, may be provided to the machine learning model 404 as input, i.e., the additional data may be represented in features of a feature vector input to the model. To train the machine learning model 404, this additional data may also be collected from the users of the user population 304. Accordingly, the user interface 804 may be displayed to the users of the user population 304 to collect this additional data from those users, e.g., data describing demographics, medical history, exercise, and/or stress.

In the illustrated example 800, the user interface 800 includes a variety of graphical elements with which a user may interact (e.g., select or enter values) to provide additional data about him- or her-self. However, it is to be appreciated that the included graphical elements are merely examples, and a user interface to collect such additional data may be configured in different ways to include more, fewer, or different elements that enable collection of various additional data without departing from the spirit or scope of the described techniques.

Having discussed examples of details of the techniques for diabetes prediction using glucose measurements and machine learning, consider now some examples of procedures to illustrate additional aspects of the techniques.

Examples of Procedures

This section describes examples of procedures for diabetes prediction using glucose measurements and machine learning. Aspects of the procedures may be implemented in hardware, firmware, or software, or a combination thereof. The procedures are shown as a set of blocks that specify operations performed by one or more devices and are not necessarily limited to the orders shown for performing the operations by the respective blocks. In at least some implementations the procedures are performed by a prediction system, such as the prediction system 114 that makes use of the preprocessing manager 402, the machine learning model 404, and the model manager 502.

Figure 9:
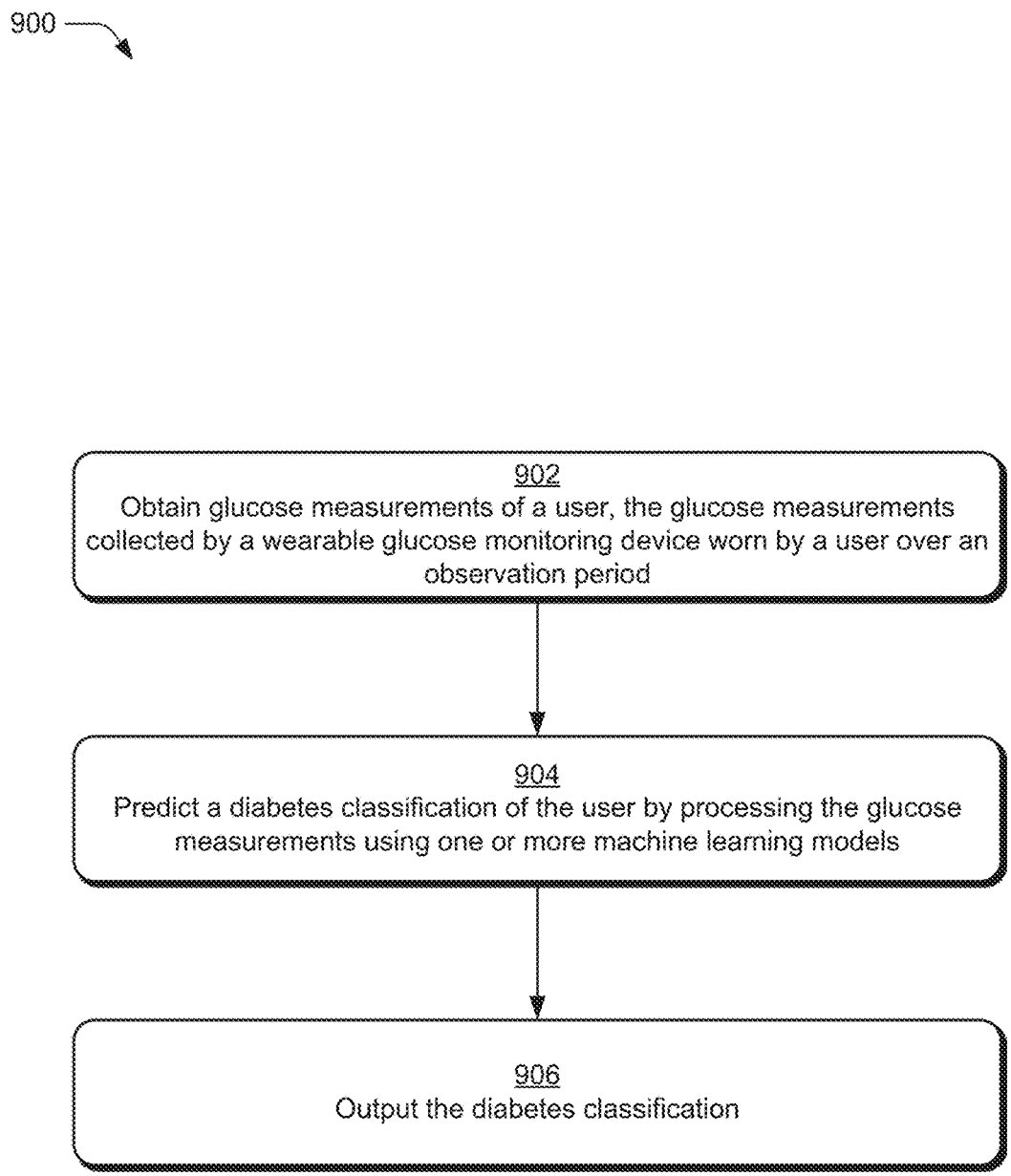
FIG. 9 depicts a procedure in an example of an implementation in which a machine learning model predicts a diabetes classification based on glucose measurements of a user collected by a wearable glucose monitoring device during an observation period.

FIG. 9 depicts a procedure 900 in an example of an implementation in which a machine learning model predicts a diabetes classification based on glucose measurements of a user collected by a wearable glucose monitoring device during an observation period.

Glucose measurements of a user are obtained (block 902). In accordance with the principles discussed herein, the glucose measurements are collected by a wearable glucose monitoring device during an observation period. By way of example, the machine learning model 404 obtains glucose measurements 110 of a user which are collected by the wearable glucose monitoring device 104 worn by the person 102 during an observation period. The wearable glucose monitoring device 104 may be provided as part of an observation kit, for instance, for the purpose of monitoring the person 102's glucose. Regardless of how the wearable glucose monitoring device 104 is obtained by the person 102, the device is configured to monitor glucose of the person 102 during an observation period, which lasts for a time period generally spanning multiple days. The wearable glucose monitoring device 104 may be configured with a sensor 202, for instance, which may be inserted subcutaneously into skin of the person 102 and used to measure glucose in the person 102's blood.

Although discussed throughout as being inserted subcutaneously into the person 102's skin, in one or more implementations, the sensor 202 may not be inserted subcutaneously. In such implementations, the sensor 202 may instead be disposed on the person 102's skin or muscle. For example, the sensor 202 may be a patch that adheres to the person 102's skin for a period of time. This patch may then be peeled off. Alternately or additionally, a non-invasive glucose sensor may be optical based, e.g., using photoplethysmography (PPG). The sensor 202 may be configured in a variety of ways to obtain measurements indicative of a person 102's glucose without departing from the spirit or scope of the described techniques.

A diabetes classification of the user is predicted by processing the glucose measurements using one or more machine learning models (block 904). In accordance with the principles discussed herein, the one or more machine learning models are generated based on historical glucose measurements and historical outcome data of a user population. By way of example, the machine learning model 404 predicts the diabetes classification 116. The machine learning model 404 generates this prediction by processing the glucose measurements 110 based on patterns, learned during training, of the glucose measurements 110 and outcome data 306 of the user population 304. As noted above, the user population 304 includes users that wear wearable glucose monitoring devices, such as the wearable glucose monitoring device 104.

The diabetes classification is output (block 906). By way of example, the machine learning model 404 outputs the diabetes classification 116. As discussed throughout, the diabetes classification 116 may indicate whether it is predicted the person has diabetes or is predicted to experience adverse effects associated with diabetes. The diabetes classification 116 may also be used to generate one or more notifications or user interfaces based on the classification, such as a report directed to a health care provider that includes the diabetes classification (e.g., that the person is predicted to have diabetes) or a notification directed to the person 102 that instructs the person to contact his or her health care provider.

Figure 10:
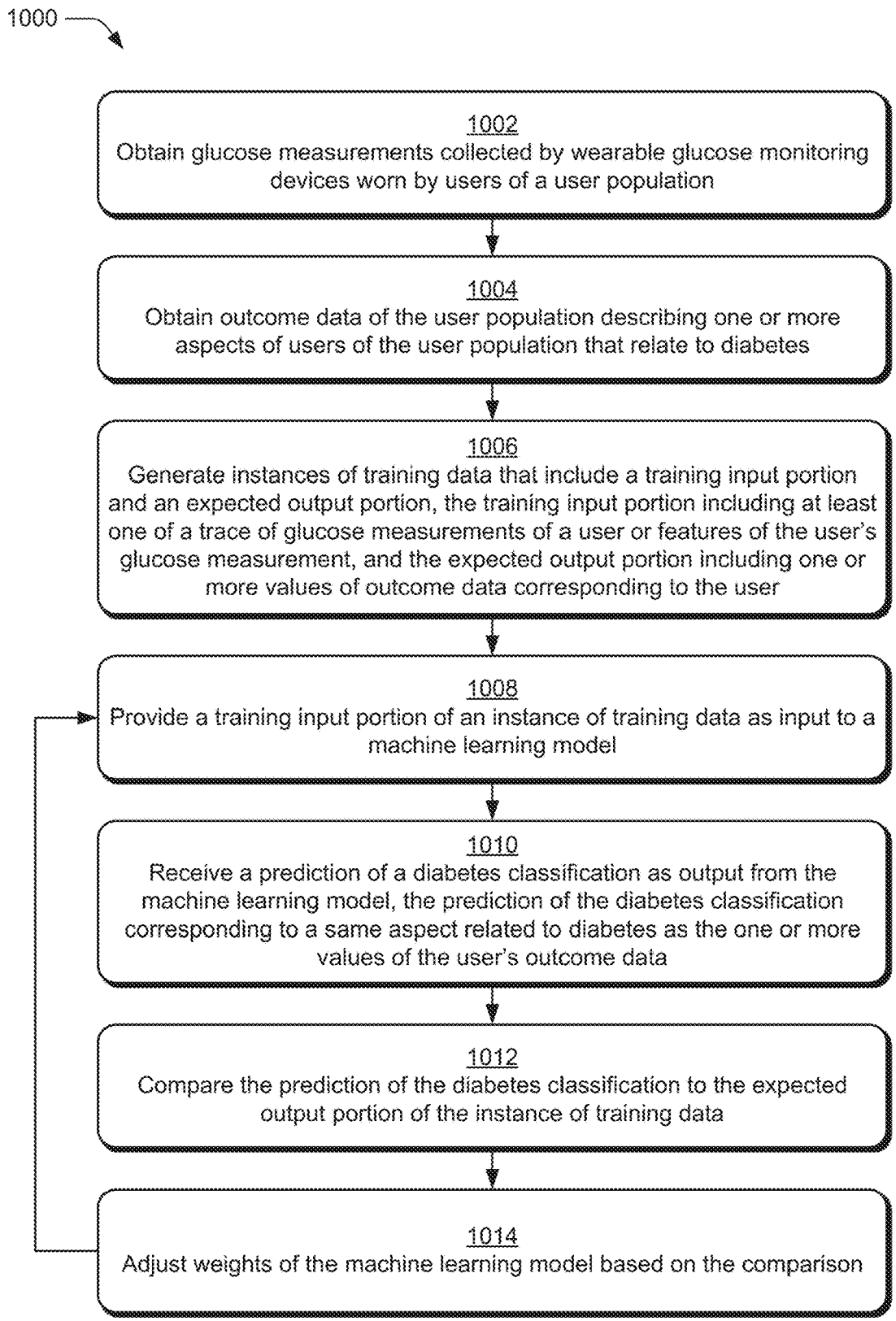
FIG. 10 depicts a procedure in an example of an implementation in which a machine learning model is trained to predict a diabetes classification based on historical glucose measurements and outcome data of a user population.

FIG. 10 depicts a procedure 1000 in an example of an implementation in which a machine learning model is trained to predict a diabetes classification based on historical glucose measurements and outcome data of a user population.

Glucose measurements collected by wearable glucose monitoring devices worn by users of a user population are obtained (block 1002). By way of example, the model manager 502 obtains the glucose measurements 110 of users of the user population 304. Outcome data is obtained that describes one or more aspects of users of the user population that relate to diabetes (block 1004). By way of example, the model manager 502 obtains the outcome data 306. In the examples discussed above, the outcome data describes example aspects, such as one or more of the independent diagnostic measures 308 of the users of the user population 304, the observed adverse effects 310 of the users of the user population 304, and the clinical diagnoses 312 of the users of the user population 304.

Instances of training data are generated that include a training input portion and an expected output portion (block 1006). In accordance with the principles discussed herein, the training input portion includes at least one of a trace of glucose measurements of a user or features of the user's glucose measurements. Further, the expected output portion includes one or more values of the outcome data that corresponds to the user. By way of example, the model manager 502 generates instances of training data by associating the trace of glucose measurements or the features of the user's glucose measurements obtained at block 1002 with the one or more values of the user's outcome data obtained at block 1004. In one or more implementations, the model manager 502 "labels" the trace of glucose measurements or the features of the user's glucose measurements with one or more labels representative of the values of the outcome data corresponding to the user.

Here, blocks 1008-1014 may be repeated until a machine learning model is suitably trained, such as until the machine learning model "converges" on a solution, e.g., the internal weights of the model have been suitably adjusted due to training iterations so that the model consistently generates predictions that substantially match the expected output portions. Alternately or in addition, the blocks 1008-1014 may be repeated for a number of instances (e.g., all instances) of the training data.

A training input portion of an instance of training data is provided as input to the machine learning model (block 1008). By way of example, the model manager 502 provides a training input portion of an instance of training data generated at block 1006 as input to the machine learning model 404.

A prediction of a diabetes classification is received as output from the machine learning model (block 1010). In accordance with the principles discussed herein, the prediction of the diabetes classification corresponds to a same aspect related to diabetes as the one or more values of the user's outcome data included in the training instance. By way of example, the machine learning model 404 predicts a diabetes classification (e.g., a classification of the user in a 'diabetes' class, a 'prediabetes' class, or a 'no diabetes class' or a value indicative of one of those classes) based on the training input portion provided at block 1008, and the model manager 502 receives the diabetes classification as output of the machine learning model 404.

The prediction of the diabetes classification is compared to the expected output portion of the instance of training data (block 1012). By way of example, the model manager 502 compares the diabetes classification predicted at block 1010 to the expected output portion of the training instance generated at block 1006, e.g., by using a loss function such as mean squared error (MSE). It is to be appreciated that the model manager 502 may use other loss functions during training, to compare the predictions of the machine learning model 404 to the expected output, without departing from the spirit or scope of the described techniques.

Weights of the machine learning model are adjusted based on the comparison (block 1014). By way of example, the model manager 502 may adjust internal weights of the machine learning model 404 based on the comparing. In one or more implementations, the model manager 502 may optionally leverage one or more hyperparameter optimization techniques during training to tune hyperparameters of the learning algorithm employed.

Having described examples of procedures in accordance with one or more implementations, consider now an example of a system and device that can be utilized to implement the various techniques described herein.

Example of a System and Device

Figure 11:
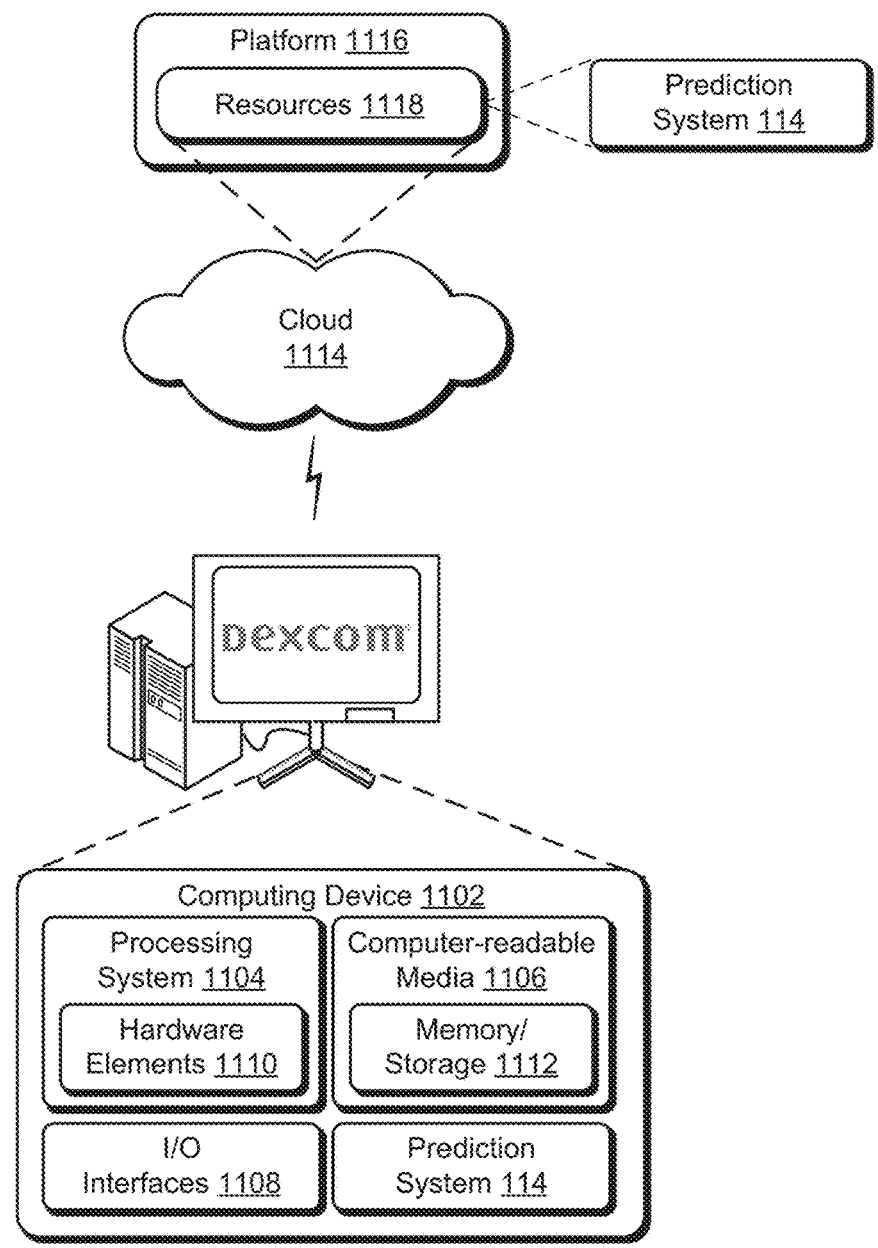
FIG. 11 illustrates an example of a system including various components of an example of a device that can be implemented as any type of computing device as described and/or utilized with reference to FIGS. 1-10 to implement embodiments of the techniques described herein.

FIG. 11 illustrates an example of a system generally at 1100 that includes an example of a computing device 1102 that is representative of one or more computing systems and/or devices that may implement the various techniques described herein. This is illustrated through inclusion of the prediction system 114 at the platform level as well as at the individual computing device level. The prediction system 114 may be implemented at one level or the other or at least partially at both levels. The computing device 1102 may be, for example, a server of a service provider, a device associated with a client (e.g., a client device), an on-chip system, and/or any other suitable computing device or computing system.

The example of the computing device 1102 as illustrated includes a processing system 1104, one or more computer-readable media 1106, and one or more I/O interfaces 1108 that are communicatively coupled, one to another. Although not shown, the computing device 1102 may further include a system bus or other data and command transfer system that couples the various components, one to another. A system bus can include any one or combination of different bus structures, such as a memory bus or memory controller, a peripheral bus, a universal serial bus, and/or a processor or local bus that utilizes any of a variety of bus architectures. A variety of other examples are also contemplated, such as control and data lines.

The processing system 1104 is representative of functionality to perform one or more operations using hardware. Accordingly, the processing system 1104 is illustrated as including hardware elements 1110 that may be configured as processors, functional blocks, and so forth. This may include implementation in hardware as an application specific integrated circuit or other logic device formed using one or more semiconductors. The hardware elements 1110 are not limited by the materials from which they are formed or the processing mechanisms employed therein. For example, processors may be comprised of semiconductor(s) and/or transistors (e.g., electronic integrated circuits (ICs)). In such a context, processor-executable instructions may be electronically-executable instructions.

The computer-readable media 1106 is illustrated as including memory/storage 1112. The memory/storage 1112 represents memory/storage capacity associated with one or more computer-readable media. The memory/storage component 1112 may include volatile media (such as random access memory (RAM)) and/or nonvolatile media (such as read only memory (ROM), Flash memory, optical disks, magnetic disks, and so forth). The memory/storage component 1112 may include fixed media (e.g., RAM, ROM, a fixed hard drive, and so on) as well as removable media (e.g., Flash memory, a removable hard drive, an optical disc, and so forth). The computer-readable media 1106 may be configured in a variety of other ways as further described below.

Input/output interface(s) 1108 are representative of functionality to allow a user to enter commands and information to computing device 1102, and also allow information to be presented to the user and/or other components or devices using various input/output devices. Examples of input devices include a keyboard, a cursor control device (e.g., a mouse), a microphone, a scanner, touch functionality (e.g., capacitive or other sensors that are configured to detect physical touch), a camera (e.g., which may employ visible or non-visible wavelengths such as infrared frequencies to recognize movement as gestures that do not involve touch), and so forth. Examples of output devices include a display device (e.g., a monitor or projector), speakers, a printer, a network card, tactile-response device, and so forth. Thus, the computing device 1102 may be configured in a variety of ways as further described below to support user interaction.

Various techniques may be described herein in the general context of software, hardware elements, or program modules. Generally, such modules include routines, programs, objects, elements, components, data structures, and so forth that perform particular tasks or implement particular abstract data types. The terms "module," "functionality," and "component" as used herein generally represent software, firmware, hardware, or a combination thereof. The features of the techniques described herein are platform-independent, meaning that the techniques may be implemented on a variety of commercial computing platforms having a variety of processors.

An implementation of the described modules and techniques may be stored on or transmitted across some form of computer-readable media. The computer-readable media may include a variety of media that may be accessed by the computing device 1102. By way of example, and not limitation, computer-readable media may include "computer-readable storage media" and "computer-readable signal media."

"Computer-readable storage media" may refer to media and/or devices that enable persistent and/or non-transitory storage of information in contrast to mere signal transmission, carrier waves, or signals per se. Thus, computer-readable storage media refers to non-signal bearing media. The computer-readable storage media includes hardware such as volatile and non-volatile, removable and non-removable media and/or storage devices implemented in a method or technology suitable for storage of information such as computer readable instructions, data structures, program modules, logic elements/circuits, or other data. Examples of computer-readable storage media may include, but are not limited to, RAM, ROM, EEPROM, flash memory or other memory technology, CD-ROM, digital versatile disks (DVD) or other optical storage, hard disks, magnetic cassettes, magnetic tape, magnetic disk storage or other magnetic storage devices, or other storage device, tangible media, or article of manufacture suitable to store the desired information and which may be accessed by a computer.

"Computer-readable signal media" may refer to a signal-bearing medium that is configured to transmit instructions to the hardware of the computing device 1102, such as via a network. Signal media typically may embody computer readable instructions, data structures, program modules, or other data in a modulated data signal, such as carrier waves, data signals, or other transport mechanism. Signal media also include any information delivery media. The term "modulated data signal" means a signal that has one or more of its characteristics set or changed in such a manner as to encode information in the signal. By way of example, and not limitation, communication media include wired media such as a wired network or direct-wired connection, and wireless media such as acoustic, RF, infrared, and other wireless media.

As previously described, hardware elements 1110 and computer-readable media 1106 are representative of modules, programmable device logic and/or fixed device logic implemented in a hardware form that may be employed in some embodiments to implement at least some aspects of the techniques described herein, such as to perform one or more instructions. Hardware may include components of an integrated circuit or on-chip system, an application-specific integrated circuit (ASIC), a field-programmable gate array (FPGA), a complex programmable logic device (CPLD), and other implementations in silicon or other hardware. In this context, hardware may operate as a processing device that performs program tasks defined by instructions and/or logic embodied by the hardware as well as a hardware utilized to store instructions for execution, e.g., the computer-readable storage media described previously.

Combinations of the foregoing may also be employed to implement various techniques described herein. Accordingly, software, hardware, or executable modules may be implemented as one or more instructions and/or logic embodied on some form of computer-readable storage media and/or by one or more hardware elements 1110. The computing device 1102 may be configured to implement particular instructions and/or functions corresponding to the software and/or hardware modules. Accordingly, implementation of a module that is executable by the computing device 1102 as software may be achieved at least partially in hardware, e.g., through use of computer-readable storage media and/or hardware elements 1110 of the processing system 1104. The instructions and/or functions may be executable/operable by one or more articles of manufacture (for example, one or more computing devices 1102 and/or processing systems 1104) to implement techniques, modules, and examples described herein.

The techniques described herein may be supported by various configurations of the computing device 1102 and are not limited to the specific examples of the techniques described herein. This functionality may also be implemented all or in part through use of a distributed system, such as over a "cloud" 1114 via a platform 1116 as described below.

The cloud 1114 includes and/or is representative of a platform 1116 for resources 1118. The platform 1116 abstracts underlying functionality of hardware (e.g., servers) and software resources of the cloud 1114. The resources 1118 may include applications and/or data that can be utilized while computer processing is executed on servers that are remote from the computing device 1102. Resources 1118 can also include services provided over the Internet and/or through a subscriber network, such as a cellular or Wi-Fi network.

The platform 1116 may abstract resources and functions to connect the computing device 1102 with other computing devices. The platform 1116 may also serve to abstract scaling of resources to provide a corresponding level of scale to encountered demand for the resources 1118 that are implemented via the platform 1116. Accordingly, in an interconnected device embodiment, implementation of functionality described herein may be distributed throughout the system 1100. For example, the functionality may be implemented in part on the computing device 1102 as well as via the platform 1116 that abstracts the functionality of the cloud 1114.

CONCLUSION

Although the systems and techniques have been described in language specific to structural features and/or methodological acts, it is to be understood that the systems and techniques defined in the appended claims are not necessarily limited to the specific features or acts described. Rather, the specific features and acts are disclosed as examples of forms of implementing the claimed subject matter.

What is claimed is:

1. A method comprising:
   obtaining glucose measurements of a user, the glucose measurements collected by a wearable glucose monitoring device during an observation period spanning multiple days;
   processing the glucose measurements of the user to extract one or more glucose features;
   predicting a diabetes classification of the user by providing the one or more extracted glucose features to one or more machine learning models as input, the one or more machine learning models generated based on historical glucose measurements provided by glucose monitoring devices worn by users of a user population over respective observation periods spanning multiple days and historical outcome data of the user population; and
   outputting the diabetes classification.

2. The method as described in claim 1, wherein the diabetes classification is an indication describing a state of the user during the observation period as having one of diabetes, prediabetes, or no diabetes.

3. The method as described in claim 1, wherein the diabetes classification is an indication describing a state of the user during the observation period as having gestational diabetes or no gestational diabetes.

4. The method as described in claim 1, wherein:
   the diabetes classification is an indication of one or more adverse effects of diabetes the user is predicted to experience; and
   the historical outcome data describes adverse effects of diabetes observed in users of the user population.

5. The method as described in claim 1, wherein the wearable glucose monitoring device includes a sensor that is inserted subcutaneously into skin of the user during the observation period to collect the glucose measurements.

6. The method as described in claim 5, wherein the glucose measurements comprise time-sequenced glucose measurements collected by the wearable glucose monitoring device during the observation period.

7. The method as described in claim 6, wherein the time-sequenced glucose measurements are collected by the wearable glucose monitoring device continuously at predetermined intervals during the observation period.

8. The method as described in claim 1, further comprising:
   obtaining the historical glucose measurements and the historical outcome data of the user population, the historical glucose measurements provided by glucose monitoring devices worn by users of the user population; and
   generating the one or more machine learning models by providing the historical glucose measurements to the one or more machine learning models, comparing training classifications of diabetes received from the one or more machine learning models to diabetes classifications indicated by the historical outcome data, and adjusting weights of the one or more machine learning models.

9. The method as described in claim 8, further comprising labeling traces of the historical glucose measurements with labels indicative of a respective user's diabetes classification based on the historical outcome data.

10. The method as described in claim 8, wherein the historical outcome data is associated with one or more diagnostic measures independent of the historical glucose measurements provided by the glucose monitoring devices worn by users of the user population.

11. The method as described in claim 1, wherein the historical outcome data includes labels of traces of the historical glucose measurements that indicate whether a respective user of the user population is clinically diagnosed with diabetes based on one or more diagnostic measures.

12. The method as described in claim 11, wherein the one or more diagnostic measures include at least one of Hemoglobin A1c (HbA1c), an Oral Glucose Tolerance Test (OGTT), or Fasting Plasma Glucose (FPG).

13. The method as described in claim 1, wherein the one or more extracted glucose features include at least one of:
   a time over threshold measure corresponding to an amount of time during the observation period that the glucose measurements of the user are above a glucose threshold;
   a time within range measure corresponding to an amount of time during the observation period that the user's glucose measurements of the user are between a first glucose level and a second glucose level that is less than the first glucose level;
   a rate-of-change measure corresponding to a difference in glucose measurements over a unit of time;
   a mean glucose measure; or
   a median glucose measure.

14. The method as described in claim 1, wherein the machine learning model predicts the diabetes classification of the user using at least two extracted glucose features.

15. The method as described in claim 1, wherein the processing further comprises filtering the glucose measurements by removing at least a portion of the glucose measurements and extracting the one or more glucose features from the filtered glucose measurements.

16. The method as described in claim 1, wherein the outputting comprises outputting a glucose observation report that includes the diabetes classification and at least one of:
   one or more treatment recommendations for the user based on the diabetes classification;
   a visual representation of the glucose measurements collected by the glucose monitoring device during the observation period; or
   one or more glucose statistics of the user generated based on the glucose measurements collected by the glucose monitoring device during the observation period.

17. The method as described in claim 16, wherein the one or more glucose statistics include at least one of:
   a time over threshold measure corresponding to an amount of time during the observation period that the glucose measurements of the user are above a glucose threshold;
   a time within range measure corresponding to an amount of time during the observation period that the user's glucose measurements of the user are between a first glucose level and a second glucose level that is less than the first glucose level;

a rate-of-change measure corresponding to a difference in glucose measurements over a unit of time;

a mean glucose measure; or a median glucose measure.

18. The method as described in claim 1, wherein the glucose measurements are obtained from a storage of the glucose monitoring device or from one or more data packets containing the glucose measurements communicated from the glucose monitoring device over a network.

19. A device comprising:

one or more processors; and memory having stored thereon computer-readable instructions that are executable by the one or more processors to perform operations comprising:

obtaining glucose measurements of a user, the glucose measurements collected by a wearable glucose monitoring device during an observation period spanning multiple days;

processing the glucose measurements of the user to extract one or more glucose features;

predicting a diabetes classification of the user by providing the one or more extracted glucose features to one or more machine learning models as input, the one or more machine learning models generated based on historical glucose measurements provided by glucose monitoring devices worn by users of a user population over respective observation periods spanning multiple days and historical outcome data of the user population; and outputting the diabetes classification.

20. The device as described in claim 19, wherein the diabetes classification is an indication describing a state of the user during the observation period as having one of diabetes, prediabetes, or no diabetes.

21. The device as described in claim 19, wherein:

the diabetes classification is an indication of one or more adverse effects of diabetes the user is predicted to experience; and the historical outcome data describes adverse effects of diabetes observed in users of the user population.

22. One or more non-transitory computer-readable storage media having instructions stored thereon that are executable by one or more processors to perform operations comprising:

obtaining glucose measurements of a user, the glucose measurements collected by a wearable glucose monitoring device during an observation period spanning multiple days;

processing the glucose measurements of the user to extract one or more glucose features;

predicting a diabetes classification of the user by providing the one or more extracted glucose features to one or more machine learning models as input, the one or more machine learning models generated based on historical glucose measurements provided by glucose monitoring devices worn by users of a user population over respective observation periods spanning multiple days and historical outcome data of the user population; and outputting the diabetes classification.

23. The one or more non-transitory computer-readable storage media as described in claim 22, wherein the diabetes classification is an indication describing a state of the user during the observation period as having one of diabetes, prediabetes, or no diabetes.

24. The one or more non-transitory computer-readable storage media as described in claim 22, wherein:

the diabetes classification is an indication of one or more adverse effects of diabetes the user is predicted to experience; and the historical outcome data describes adverse effects of diabetes observed in users of the user population.

25. An apparatus comprising:

an obtaining means for obtaining glucose measurements of a user, the glucose measurements collected by a wearable glucose monitoring device during an observation period spanning multiple days;

a processing means for processing the glucose measurements of the user to extract one or more glucose features;

a predicting means for predicting a diabetes classification of the user by providing the one or more extracted glucose features to using one or more machine learning models, the one or more machine learning models generated based on historical glucose measurements provided by glucose monitoring devices worn by users of a user population over respective observation periods spanning multiple days and historical outcome data of a user population; and an outputting means for outputting the diabetes classification.

26. A system comprising:

a wearable glucose monitoring device comprising a sensor to collect glucose measurements of a user during an observation period spanning a plurality of days, the sensor inserted subcutaneously into skin of the user during the observation period spanning the plurality of days;

a storage device to maintain the glucose measurements of the user collected during the observation period; and a prediction system to obtain the glucose measurements of the user collected during the observation period, and predict a diabetes classification of the user by processing the glucose measurements of the user to extract one or more glucose features and providing the one or more extracted glucose features to one or more machine learning models as input, wherein the one or more machine learning models are generated based on historical glucose measurements provided by glucose monitoring devices worn by users of a user population over respective observation periods spanning multiple days and historical outcome data of the user population.

27. The system as described in claim 26, further comprising a model manager to:

obtain the historical glucose measurements and the historical outcome data of the user population, the historical glucose measurements provided by glucose monitoring devices worn by users of the user population; and generate the one or more machine learning models by providing the historical glucose measurements to the one or more machine learning models, comparing training classifications of diabetes received from the one or more machine learning models to diabetes classifications indicated by the historical outcome data, and adjusting weights of the one or more machine learning models.

28. The system as described in claim 27, wherein the historical outcome data is associated with one or more diagnostic measures independent of the historical glucose measurements provided by the glucose monitoring devices worn by users of the user population.

29. The system as described in claim 27, wherein the glucose monitoring device is configured differently than the glucose monitoring devices worn by the users of the user population which provide the historical glucose measurements.

30. The system as described in claim 29, wherein the wearable glucose monitoring device is configured to prevent the user from viewing the collected glucose measurements during the observation period.

31. The system as described in claim 29, wherein the storage device is implemented at the wearable glucose monitoring device, and wherein the storage device is configured to maintain a greater number of glucose measurements than a storage of the glucose monitoring devices worn by the users of the user population.

32. The system as described in claim 26, wherein the prediction system is implemented at one or more computing devices remote from the glucose monitoring device.

33. The system as described in claim 26, wherein the prediction system is implemented, at least in part, at the wearable glucose monitoring device.

34. A method comprising:
obtaining glucose measurements collected by wearable glucose monitoring devices worn by users of a user population over observation periods spanning multiple days;
obtaining outcome data of the user population describing one or more aspects of users of the user population that relate to diabetes;
generating instances of training data that include a training input portion and an expected output portion, the training input portion including at least a feature of a user's glucose measurements, and the expected output portion including one or more values of outcome data corresponding to the user; and
training a machine learning model to predict a diabetes classification by:
providing a training input portion of an instance of training data as input to the machine learning model;
receiving a prediction of a diabetes classification as output from the machine learning model, the prediction of the diabetes classification corresponding to a same aspect related to diabetes as the one or more values of the user's outcome data;
comparing the prediction of the diabetes classification to the expected output portion of the instance of training data; and
adjusting weights of the machine learning model.

35. The method as described in claim 34, wherein the outcome data is associated with one or more diagnostic measures independent of the glucose measurements collected by the glucose monitoring devices worn by users of the user population.

36. The method as described in claim 34, wherein the diabetes classification describes a state of the user as having one of diabetes, prediabetes, or no diabetes.

37. The method as described in claim 34, wherein the diabetes classification describes a state of the user as having gestational diabetes or no gestational diabetes.

* * * * *